United States Patent
Masui et al.

(10) Patent No.: US 11,620,857 B2
(45) Date of Patent: Apr. 4, 2023

(54) METHOD, DEVICE, AND MEDIUM FOR DETERMINING THREE-DIMENSIONAL POSITION OF SKELETON USING DATA ACQUIRED BY MULTIPLE SENSORS

(71) Applicant: FUJITSU LIMITED, Kawasaki (JP)

(72) Inventors: Shoichi Masui, Sagamihara (JP); Hiroaki Fujimoto, Nakahara (JP)

(73) Assignee: FUJITSU LIMITED, Kawasaki (JP)

( * ) Notice: Subject to any disclaimer, the term of this patent is extended or adjusted under 35 U.S.C. 154(b) by 170 days.

(21) Appl. No.: 16/824,707

(22) Filed: Mar. 20, 2020

(65) Prior Publication Data

US 2020/0218889 A1 Jul. 9, 2020

Related U.S. Application Data

(63) Continuation of application No. PCT/JP2017/035915, filed on Oct. 3, 2017.

(51) Int. Cl.
*G06K 9/00* (2022.01)
*G06V 40/20* (2022.01)
(Continued)

(52) U.S. Cl.
CPC .......... *G06V 40/20* (2022.01); *A63B 24/0062* (2013.01); *G06T 7/55* (2017.01);
(Continued)

(58) Field of Classification Search
CPC ........ G06V 40/20; G06V 20/64; G06V 40/23; A63B 24/0062; A63B 71/0622;
(Continued)

(56) References Cited

U.S. PATENT DOCUMENTS

| 2005/0078178 A1* | 4/2005 | Brown | H04N 7/181 |
| | | | 348/139 |
| 2010/0197390 A1 | 8/2010 | Craig et al. | |

(Continued)

FOREIGN PATENT DOCUMENTS

| JP | 2010-061376 A | 3/2010 |
| JP | 2015-167008 A | 9/2015 |

(Continued)

OTHER PUBLICATIONS

Azrour, Samir, Sébastien Piérard, and M. Van Droogenbroeck. "Leveraging orientation knowledge to enhance human pose estimation methods." International Conference on Articulated Motion and Deformable Objects. Springer, Cham, 2016. (Year: 2016).*

(Continued)

*Primary Examiner* — Andrew M Moyer
(74) *Attorney, Agent, or Firm* — Xsensus LLP

(57) ABSTRACT

A recognition method executed by a processor, includes: acquiring positional relation between a plurality of sensors each of which senses a distance to an object; provisionally classifying an orientation of the object relative to each individual sensor included in the sensors into one of a plurality of classifications based on sensing data acquired by the individual sensor; calculating likelihood of each combination corresponding to the positional relation between the sensors based on a result of provisional classification of the orientation of the object relative to the individual sensor; and classifying the orientation of the object corresponding to each individual sensor in accordance with the calculated likelihood of each combination.

7 Claims, 22 Drawing Sheets

(51) Int. Cl.
*G06T 7/55* (2017.01)
*G06T 7/70* (2017.01)
*A63B 24/00* (2006.01)
*G06V 20/64* (2022.01)
*A61B 5/11* (2006.01)
*A63B 71/06* (2006.01)

(52) U.S. Cl.
CPC ............... *G06T 7/70* (2017.01); *G06V 20/64* (2022.01); *A61B 5/1123* (2013.01); *A63B 71/0622* (2013.01); *A63B 2024/0071* (2013.01); *A63B 2071/0647* (2013.01); *A63B 2220/05* (2013.01); *A63B 2220/20* (2013.01); *A63B 2220/803* (2013.01); *G06T 2207/30196* (2013.01)

(58) Field of Classification Search
CPC .... A63B 2024/0071; A63B 2071/0647; A63B 2220/05; A63B 2220/20; A63B 2220/803; G06T 7/55; G06T 7/70; G06T 2207/30196; G06T 7/73; G06T 2207/10028; G06T 2207/30221; A61B 5/1123; A61B 5/0077; A61B 5/1114; A61B 5/1116; A61B 5/1122; A61B 5/1128; A61B 5/6889; A61B 5/7267
See application file for complete search history.

(56) References Cited

U.S. PATENT DOCUMENTS

2015/0036879 A1    2/2015   Shiozaki et al.
2019/0156564 A1    5/2019   Tung

FOREIGN PATENT DOCUMENTS

| JP | 2016-081121 A | 5/2016 |
| JP | 6116784 B1 | 4/2017 |
| JP | 2017-091377 A | 5/2017 |
| WO | 2010/112320 A1 | 10/2010 |

OTHER PUBLICATIONS

International Search Report and Written Opinion dated Dec. 26, 2017 for PCT/JP2017/035915 filed on Oct. 3, 2017, 8 pages including English Translation of the International Search Report.

Kamijo, S., "Human Posture Recognition and Tracking for Marketing Video with Consideration of Relationship between Parameters for Retail Surveillance Videos," Image Laboratory, vol. 25 No. 3, 12 pages.

Partial Supplementary European Search Report dated Aug. 12, 2020, issued in corresponding European Patent Application No. 17927898.1.

Edouard Auvinet et al: "Multiple depth cameras calibration and body volume reconstruction for gait analysis", Information Science, Signal Processing and Their Applications (ISSPA), 2012 11th International Conference on, IEEE, Jul. 2, 2012 (Jul. 2, 2012), pp. 478-483, XP032241695.

Voit Michael et al: "Estimating the Lecturer's Head Pose in Seminar Scenarios—A Multi-view Approach", Jul. 11, 2005 (Jul. 11, 2005), Ann Ual International Con Ference on The Theory and Applications of Cryptographic Techniques, Eurocrypt 2018; [Lecture Notes in Computer Science; Lect. Notes Computer], Springer, Berlin, Heidelberg, pp. 230-240, XP047448989.

Gabriele Fanelli et al: "Real Time Head Pose Estimation from Consumer Depth Cameras", Aug. 31, 2011 (Aug. 31, 2011), Pattern Recognition, Springer Berlin Heidelberg, Berlin, Heidelberg, pp. 101-110, XP019163424.

Fitte-Duval Laurent et al: "Combination of RGB-D Features for Head and Upper Body Orientation Classification", Oct. 21, 2016 (Oct. 21, 2016), Annual International Conference on The Theory and Applications of Cryptographic Techniques, Eurocrypt 2018; [Lecture Notes in Computer Science; Lect.Notes Computer], Springer, Berlin, Heidelberg, pp. 591-603, XP047360172.

\* cited by examiner

| SPIN DIRECTION | HANDSTAND DIRECTION |
|---|---|
| 1-5 | 1-1 |
| 2-6 | 2-2 |
| 3-7 | 3-3 |
| 4-8 | 4-4 |
| 5-9 | 5-5 |
| 6-10 | 6-6 |
| 7-11 | 7-7 |
| 8-12 | 8-8 |
| 9-1 | 9-9 |
| 10-2 | 10-10 |
| 11-3 | 11-11 |
| 12-4 | 12-12 |

METHOD, DEVICE, AND MEDIUM FOR DETERMINING THREE-DIMENSIONAL POSITION OF SKELETON USING DATA ACQUIRED BY MULTIPLE SENSORS

CROSS-REFERENCE TO RELATED APPLICATION

This application is a continuation application of International Application PCT/JP2017/035915, filed on Oct. 3, 2017 and designating the U.S., the entire contents of which are incorporated herein by reference.

FIELD

The present invention relates to a recognition program, a recognition method, and a recognition device.

BACKGROUND

A conventionally available device recognizes the posture and motion of a person based on a distance image (hereinafter, also referred to as a depth image) output from a distance sensor (hereinafter, also referred to as a depth sensor) that senses the distance to the person. This device labels a site of the person based on the distance image output from, for example, one distance sensor. Subsequently, the device extracts, based on each labeled site, a skeleton model having a three-dimensional skeleton position. Thereafter, the device recognizes the posture and motion of the person based on the extracted skeleton model.
Patent Document 1: U.S. Patent No. 2010/0197390

SUMMARY

According to an aspect of the embodiments, a recognition method executed by a processor, includes: acquiring positional relation between a plurality of sensors each of which senses a distance to an object; provisionally classifying an orientation of the object relative to each individual sensor included in the sensors into one of a plurality of classifications based on sensing data acquired by the individual sensor; calculating likelihood of each combination corresponding to the positional relation between the sensors based on a result of provisional classification of the orientation of the object relative to the individual sensor; and classifying the orientation of the object corresponding to each individual sensor in accordance with the calculated likelihood of each combination.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

However, when the posture and motion of a person are to be recognized by using one distance sensor, occlusion can occur in which part of the person is hidden by, for example, an object or a site of the person. When the occlusion occurs, the accuracy of three-dimensional recognition of the skeleton of the person decreases, and it becomes difficult to recognize complicate motion. Thus, the accuracy of recognition of the skeleton of the person or the like decreases due to the occurrence of the occlusion.

In one aspect, the embodiments provide a recognition program, a recognition method, and a recognition device that can prevent recognition accuracy decrease due to the occurrence of occlusion.

An embodiment of a recognition program, a recognition method, and a recognition device disclosed by the present application will be described below in detail with reference to the accompanying drawings. The present embodiment does not limit the disclosed technology. The embodiment below may be combined as appropriate without inconsistency.

Embodiment

Figure 1:
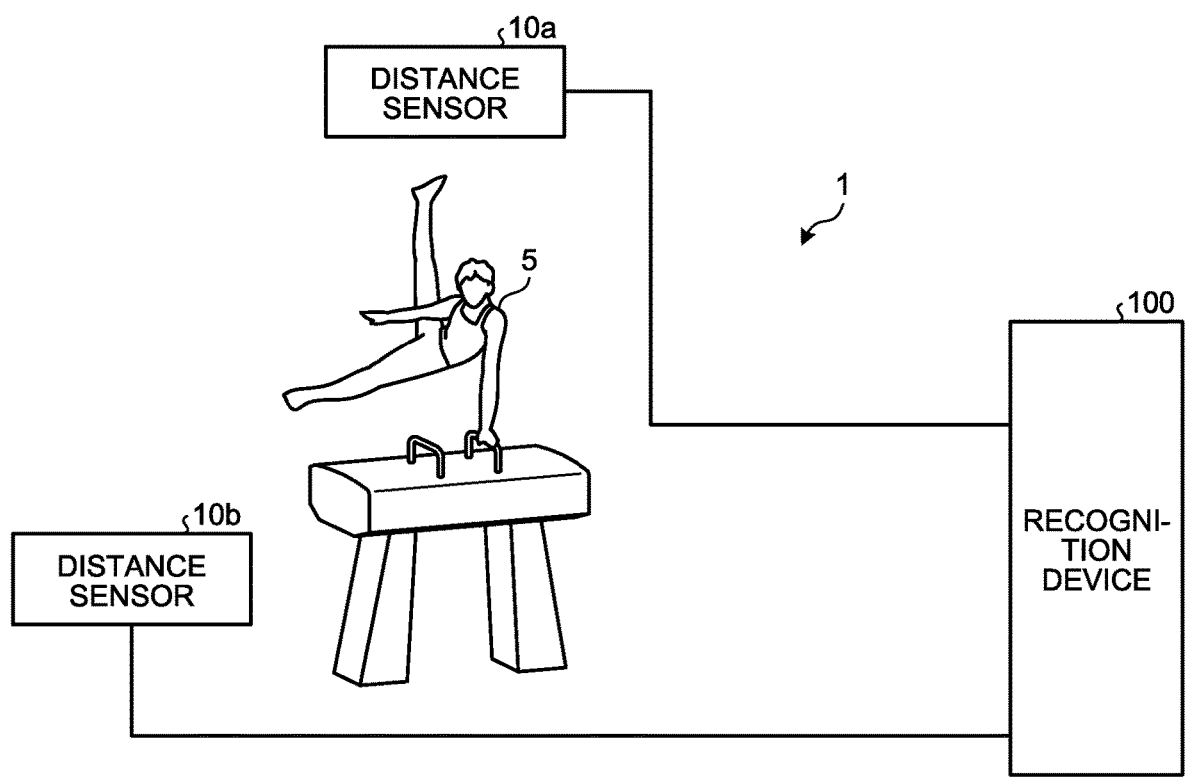
FIG. 1 is a diagram illustrating an exemplary configuration of a recognition system according to an embodiment.

FIG. 1 is a diagram illustrating an exemplary configuration of a recognition system according to an embodiment. This recognition system 1 illustrated in FIG. 1 includes distance sensors 10a and 10b and a recognition device 100. In the following description, the distance sensors 10a and 10b are simply referred to as distance sensors 10 when not distinguished from each other. The number of distance sensors 10 in the recognition system 1 is not limited, but any optional number of a plurality of distance sensors 10 may be included. The recognition device 100 and each of the distance sensors 10a and 10b are connected with each other to perform communication therebetween in a wired or wireless manner.

The recognition system 1 is an exemplary system in which a person 5 as an object is measured by each distance sensor 10 and the recognition device 100 recognizes the posture and the like of the person 5 based on a result of the measurement.

The distance sensor 10 measures (senses), for each pixel, the distance to a subject by using an infrared laser or the like, and outputs a distance image of, for example, 320×240 pixels. The distance image includes the distance and angle to each pixel. Thus, the distance image is a depth image indicating the depth of an object when viewed from the distance sensor (depth sensor) 10. The distance sensor 10 measures the distance to a subject (object) at, for example, substantially 15 m apart.

Figure 2:
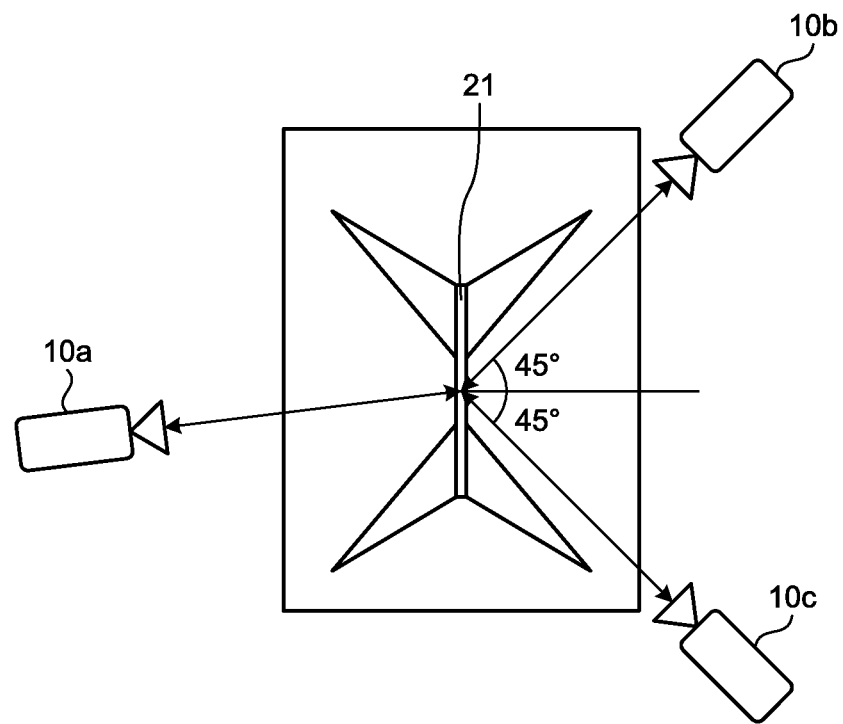
FIG. 2 is a diagram illustrating exemplary disposition of a plurality of distance sensors.
Figure 3:
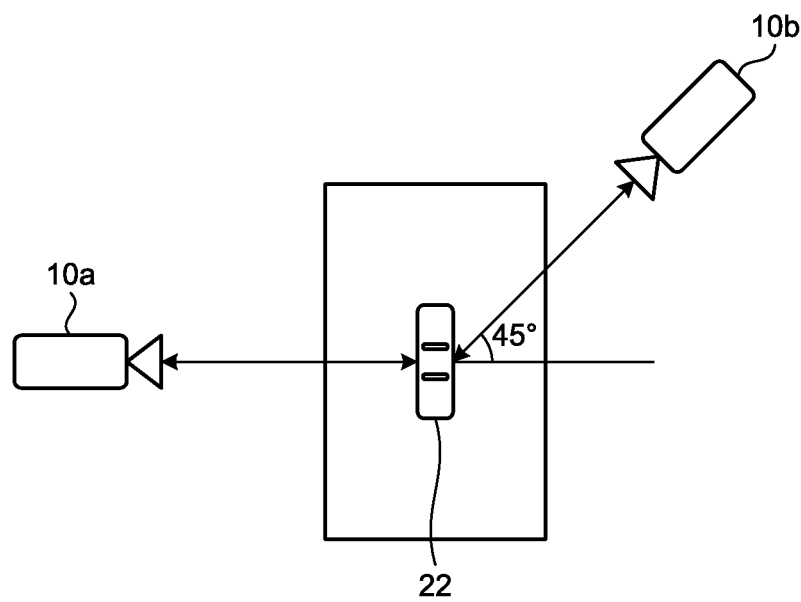
FIG. 3 is a diagram illustrating exemplary disposition of a plurality of distance sensors.

The following describes disposition of the distance sensors 10 with reference to FIGS. 2 and 3. FIGS. 2 and 3 are each a diagram illustrating exemplary disposition of a plurality of distance sensors. Each disposition is an example in gymnastics but the present invention is applicable to disposition in accordance with other sports and human motion. FIG. 2 illustrates exemplary disposition of the distance sensors 10 in a case of still rings. In the example illustrated in FIG. 2, the three distance sensors 10 are used. As illustrated in FIG. 2, a main sensor 10a is disposed at a position in the direction in which a large number of players face at still rings 21. A sub sensor 10b is disposed at a position on an obliquely back side of the still rings 21. A sub sensor 10c is disposed at a position on the obliquely back side of the still rings 21 and opposite to the sub sensor 10b.

FIG. 3 is a diagram illustrating exemplary disposition of a plurality of distance sensors. In the example illustrated in FIG. 3, the two distance sensors 10 are used. As illustrated in FIG. 3, the main sensor 10a is disposed at a position in the direction in which a player faces at a pommel horse 22. The sub sensor 10b is disposed at a position on the obliquely back side of the pommel horse 22 and oblique to an axis line of the main sensor 10a at 450 approximately.

Figure 4:
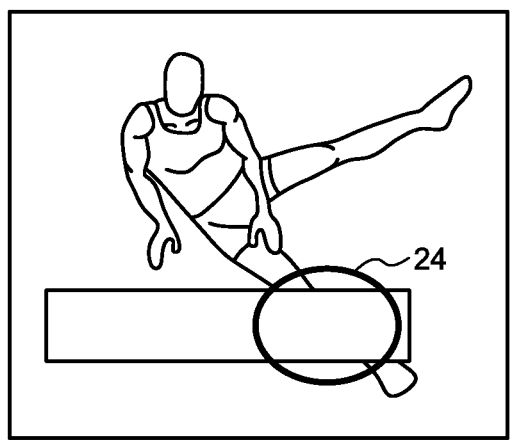
FIG. 4 is a diagram illustrating exemplary occlusion due to an object.
Figure 5:
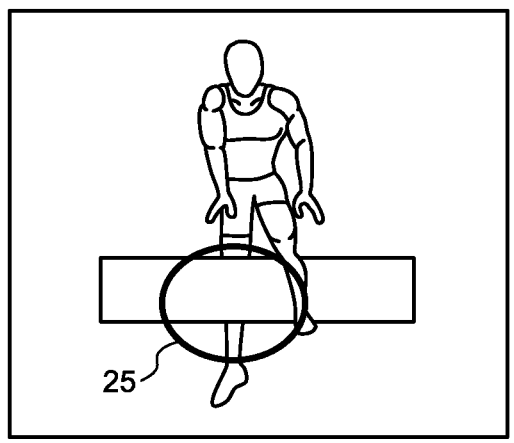
FIG. 5 is a diagram illustrating exemplary occlusion due to an object.

The following describes occlusion with reference to FIGS. 4 to 7. FIGS. 4 and 5 are each a diagram illustrating exemplary occlusion due to an object. In the occlusion illustrated in FIG. 4, part of a leg of a person performing on the pommel horse is hidden behind a pommel horse as an object as illustrated in a region 24. Similarly, in the occlusion illustrated in FIG. 5, part of a leg of a person performing on the pommel horse is hidden behind a pommel horse as an object as illustrated in a region 25.

Figure 6:
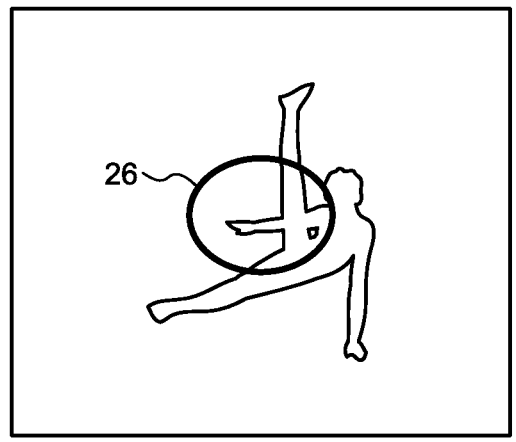
FIG. 6 is a diagram illustrating exemplary self-occlusion.
Figure 7:
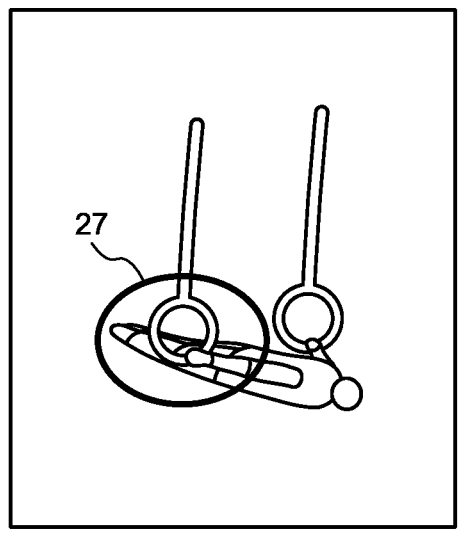
FIG. 7 is a diagram illustrating exemplary self-occlusion.

FIGS. 6 and 7 are each a diagram illustrating exemplary self-occlusion. In the occlusion illustrated in FIG. 6, part of an arm of a person performing on the pommel horse is hidden behind a leg as illustrated in a region 26. In the occlusion illustrated in FIG. 7, an arm of a person performing on still rings overlaps with the body as illustrated in a region 27.

In FIG. 1, the recognition device 100 recognizes the posture and the like of the person 5 based on distance images input from the distance sensors 10. The recognition device 100 acquires the positional relation between the distance sensors 10 each of which senses the distance to the person 5 as an object. The recognition device 100 provisionally classifies the orientation (posture) of the person 5 as an object relative to each individual distance sensor 10 included in the distance sensors 10 based on sensing data acquired by the individual distance sensor 10. The recognition device 100 calculates the likelihood of each combination corresponding to the positional relation between the distance sensors 10 based on a result of the provisional classification of the orientation of the object relative to the individual distance sensor 10. The recognition device 100 classifies the orientation (posture) of the person 5 as an object corresponding to each individual distance sensor 10 in accordance with the calculated likelihood of each combination. Accordingly, the recognition device 100 can prevent decrease of the accuracy of classification, in other words, the accuracy of recognition of the orientation (posture) of the person 5 due to the occurrence of occlusion.

The recognition device 100 acquires the positional relation between the distance sensors 10 each of which senses the distance to the person 5 as an object. The recognition device 100 acquires sensing data acquired by each individual distance sensor 10 included in the distance sensors 10. The recognition device 100 estimates the three-dimensional position of the skeleton of the object when viewed from each individual distance sensor 10 based on each acquired sensing data and a skeleton recognition dictionary selected in accordance with the orientation of the object relative to the individual distance sensor 10. The recognition device 100 determines the three-dimensional position of the skeleton of the object based on a result of the estimation of the three-dimensional position of the skeleton of the object when viewed from each individual distance sensor 10 and the positional relation between the distance sensors 10. Accordingly, the recognition device 100 can prevent recognition accuracy decrease due to the occurrence of occlusion.

Figure 8:
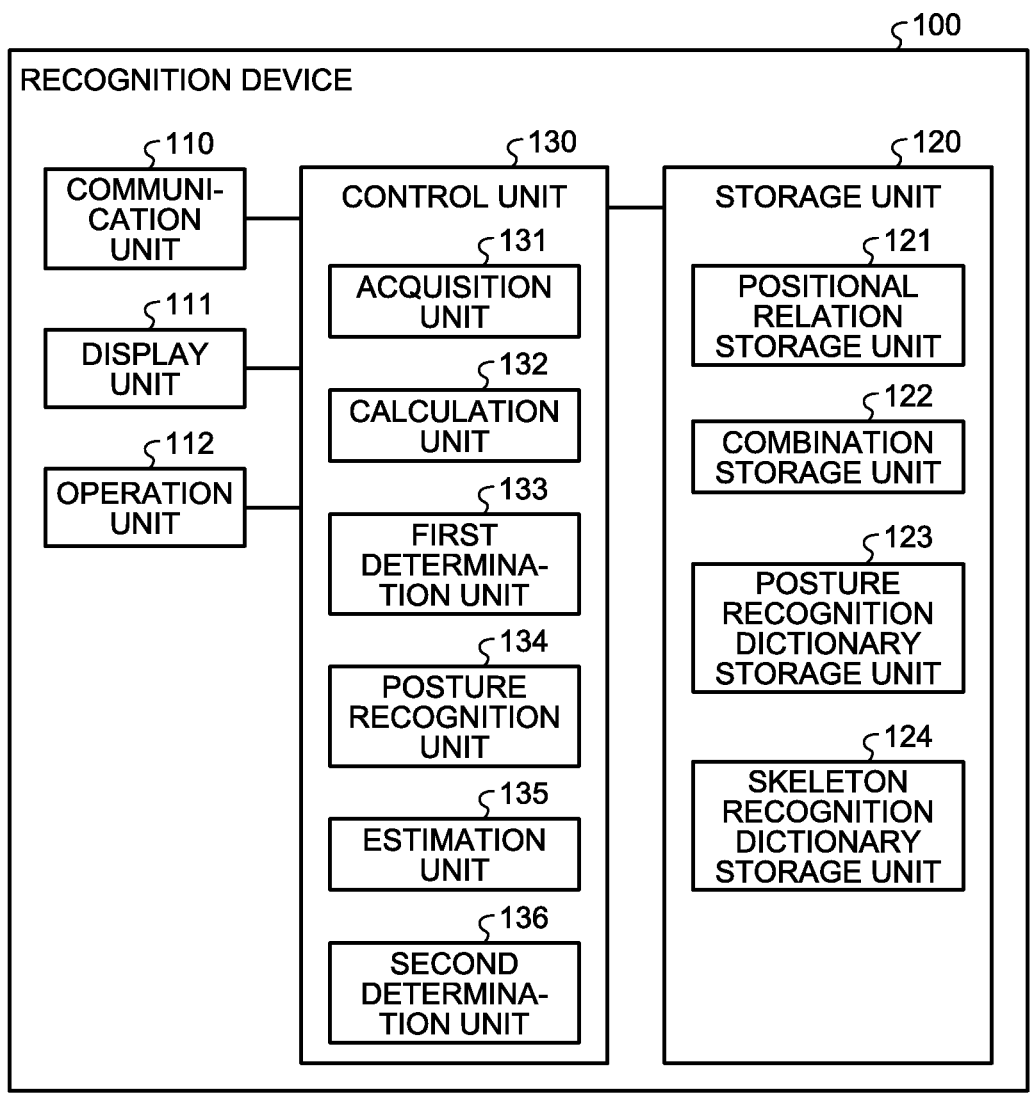
FIG. 8 is a block diagram illustrating an exemplary configuration of a recognition device according to the embodiment.

The following describes a functional configuration of the recognition device 100 with reference to FIG. 8. FIG. 8 is a block diagram illustrating an exemplary configuration of the recognition device according to the embodiment. As illustrated in FIG. 8, the recognition device 100 includes a communication unit 110, a display unit 111, an operation unit 112, a storage unit 120, and a control unit 130. The recognition device 100 may include various functional components included in a known computer, for example, functional components such as various input devices and voice output devices in addition to functional components illustrated in FIG. 8. The recognition device 100 may be, for example, a portable personal computer. The recognition device 100 may be not only the above-described portable personal computer but also a stationary personal computer.

The communication unit 110 is achieved by, for example, a network interface card (NIC). The communication unit 110 is a communication interface connected with each distance sensor 10 in a wired or wireless manner to govern information communication with the distance sensor 10.

The display unit 111 is a display device for displaying various kinds of information. The display unit 111 is achieved by, for example, a liquid crystal display as a display device. The display unit 111 displays various screens including a display screen input from the control unit 130.

The operation unit 112 is an input device that receives various operations from a user of the recognition device 100. The operation unit 112 is achieved by, for example, a keyboard or a mouse as an input device. The operation unit 112 outputs an operation input by the user to the control unit 130 as operation information. The operation unit 112 may be achieved by, for example, a touch panel as an input device, and the display device of the display unit 111 and the input device of the operation unit 112 may be integrated with each other.

The storage unit 120 is achieved by, for example, a semiconductor memory element such as a random access memory (RAM) or a flash memory, or a storage device such as a hard disk or an optical disk. The storage unit 120 includes a positional relation storage unit 121, a combination storage unit 122, a posture recognition dictionary storage unit 123, and a skeleton recognition dictionary storage unit 124. The storage unit 120 stores information used in processing at the control unit 130.

The positional relation storage unit 121 stores information related to the positional relation between the distance sensors 10. The positional relation storage unit 121 stores data of the distance sensors 10 in association with the position coordinates of a main sensor 10 from which most important information (for example, a distance image of the front of a performer) is acquired, or stores position coordinates in association with the world coordinates in association with the distance sensors 10. The positional relation storage unit 121 also stores angles in a spin direction and a handstand direction that indicate angles when a vector corresponding to each distance sensor 10 is projected onto an xz plane and a yz plane (a z axis is defined to be the distance direction from the sensor to a target, a y axis is defined to be the height direction orthogonal to the z axis, and an x axis is defined to be the horizontal direction). The spin direction is defined to be the direction of rotation about an axis from the head of the person 5 as an object toward the legs, in other words, the direction in which the person 5 twists the body while standing straight. The handstand direction is defined to be the direction in which the person 5 standing straight is inclined forward, in other words, the direction in which the person 5 performs a forward roll (somersault).

Figure 9:
FIG. 9 is a diagram illustrating an exemplary combination storage unit.

The combination storage unit 122 stores all combinations of posture numbers calculated based on each angle between the distance sensors 10. FIG. 9 is a diagram illustrating an exemplary combination storage unit. As illustrated in FIG. 9, the combination storage unit 122 includes the items of "spin direction" and "handstand direction". "Spin direction" is information indicating a combination of posture numbers of the distance sensors 10 in the spin direction. "Handstand direction" is information indicating a combination of posture numbers of the distance sensors 10 in the handstand direction.

Figure 10:
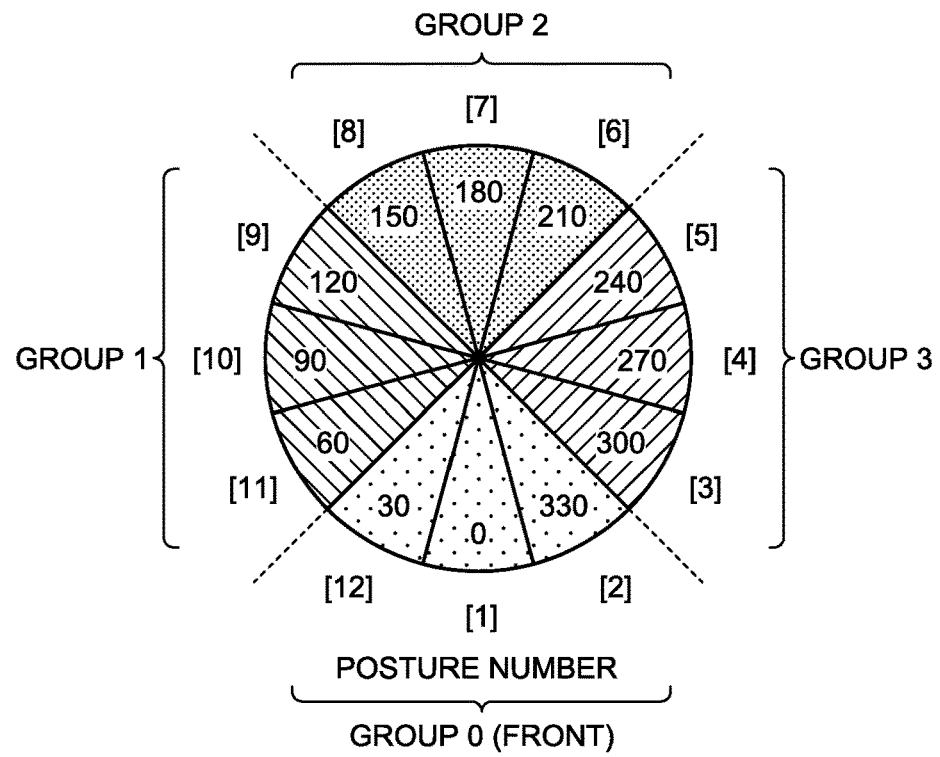
FIG. 10 is a diagram illustrating an exemplary posture recognition range and an exemplary posture recognition unit.

The following describes posture numbers with reference to FIG. 10. FIG. 10 is a diagram illustrating an exemplary posture recognition range and an exemplary posture recognition unit. As illustrated in FIG. 10, in the present embodiment, the orientation, in other words, posture of the person 5 is recognized in units of 30°. In the following description, recognition of the orientation of the person 5 is referred to as posture recognition.

In the present embodiment, the orientation of the person 5 is expressed in a posture number by dividing a circle at each 30° and allocating the posture numbers of "1" to "12" in an anticlockwise manner from the front direction of the person 5. The posture numbers are divided into groups of four directions, depending on the direction of the person 5. Group "0" is a group that corresponds to the front direction and to which Posture numbers "12", "1", and "2" belong. Group "1" is a group that corresponds to the right hand direction of the person 5 and to which Posture numbers "9", "10", and "11" belong. Group "2" is a group that corresponds to the back direction of the person 5 and to which Posture numbers "6", "7", and "8" belong. Group "3" is a group that corresponds to the left hand direction of the person 5 and on which Posture numbers "3", "4", and "5" belong.

In the example in FIG. 10, the posture recognition range corresponds to Group "0" to "3": Group "0" corresponds to the posture recognition range in the front direction, Group "1" corresponds to the posture recognition range in the right hand direction, Group "2" corresponds to the posture recognition range in the back direction, and Group "3" corresponds to the posture recognition range in the left hand direction. The skeleton recognition dictionary storage unit 124 used in skeleton recognition performs machine learning for a range expanded to the right and left from the posture recognition range by one posture number. For example, the range of skeleton recognition learning for the posture recognition range of Group "0" is the range of Posture numbers "11", "12", "1", "2", and "3". This allows the skeleton recognition to be normally performed when some error has occurred to the posture recognition.

As illustrated in FIG. 8, the posture recognition dictionary storage unit 123 stores dictionary information used to determine to which posture a distance image corresponds. The posture recognition dictionary storage unit 123 stores, for example, a posture number uniquely identifying a posture, and characteristics of a distance image corresponding to the posture number, in association with each other. The posture recognition dictionary storage unit 123 is generated by performing machine learning of various kinds of distance images. In this case, for example, random forest or deep learning may be used as an algorithm of the machine learning.

The skeleton recognition dictionary storage unit 124 is dictionary information indicating an assumed joint position (skeleton position) for each posture number (dictionary number). The skeleton recognition dictionary storage unit 124 associates, for example, a posture number, a distance image corresponding to the posture number, and information (skeleton dictionary information) of a joint position of a person. Although not illustrated, it is assumed that skeleton dictionary information corresponding to each posture number exists. Specifically, the skeleton recognition dictionary storage unit 124 is an exemplary multi-class identification device used to obtain a site label image from the distance image. The skeleton recognition dictionary storage unit 124 is generated by performing machine learning on various kinds of distance images corresponding to posture numbers and information of joint positions of a person. In this case, for example, random forest or deep learning may be used as an algorithm of the machine learning.

The control unit 130 is achieved, for example, as a computer program stored in an internal storage device is executed by a central processing unit (CPU), a graphics processing unit (GPU), or the like by using a RAM as a work area. Alternatively, the control unit 130 may be achieved by, for example, an integrated circuit such as an application specific integrated circuit (ASIC) or a field programmable gate array (FPGA).

The control unit 130 includes an acquisition unit 131, a calculation unit 132, a first determination unit 133, a posture recognition unit 134, an estimation unit 135, and a second determination unit 136, and achieves or executes functions and effects of information processing described below. Specifically, each processing unit of the control unit 130 executes first recognition processing and second recognition processing. The internal configuration of the control unit 130 is not limited to the configuration illustrated in FIG. 8 but may be any other configuration capable of performing the information processing to be described later.

The acquisition unit 131 receives and acquires the distance image (sensing data) from each distance sensor 10 through the communication unit 110. The acquisition unit 131 outputs the acquired distance image to the calculation unit 132, the posture recognition unit 134, and the estimation unit 135.

When the distance image is input from the acquisition unit 131, the calculation unit 132 converts the distance image of each distance sensor 10 into point group data. The point group data is obtained by converting each pixel of the distance image into a point expressed with the three axes of the x, y, and z axes on coordinates with respect to the individual distance sensor 10. The calculation unit 132 integrates the point group data of each distance sensor 10 after the conversion into coordinates of one coordinate system.

Figure 11:
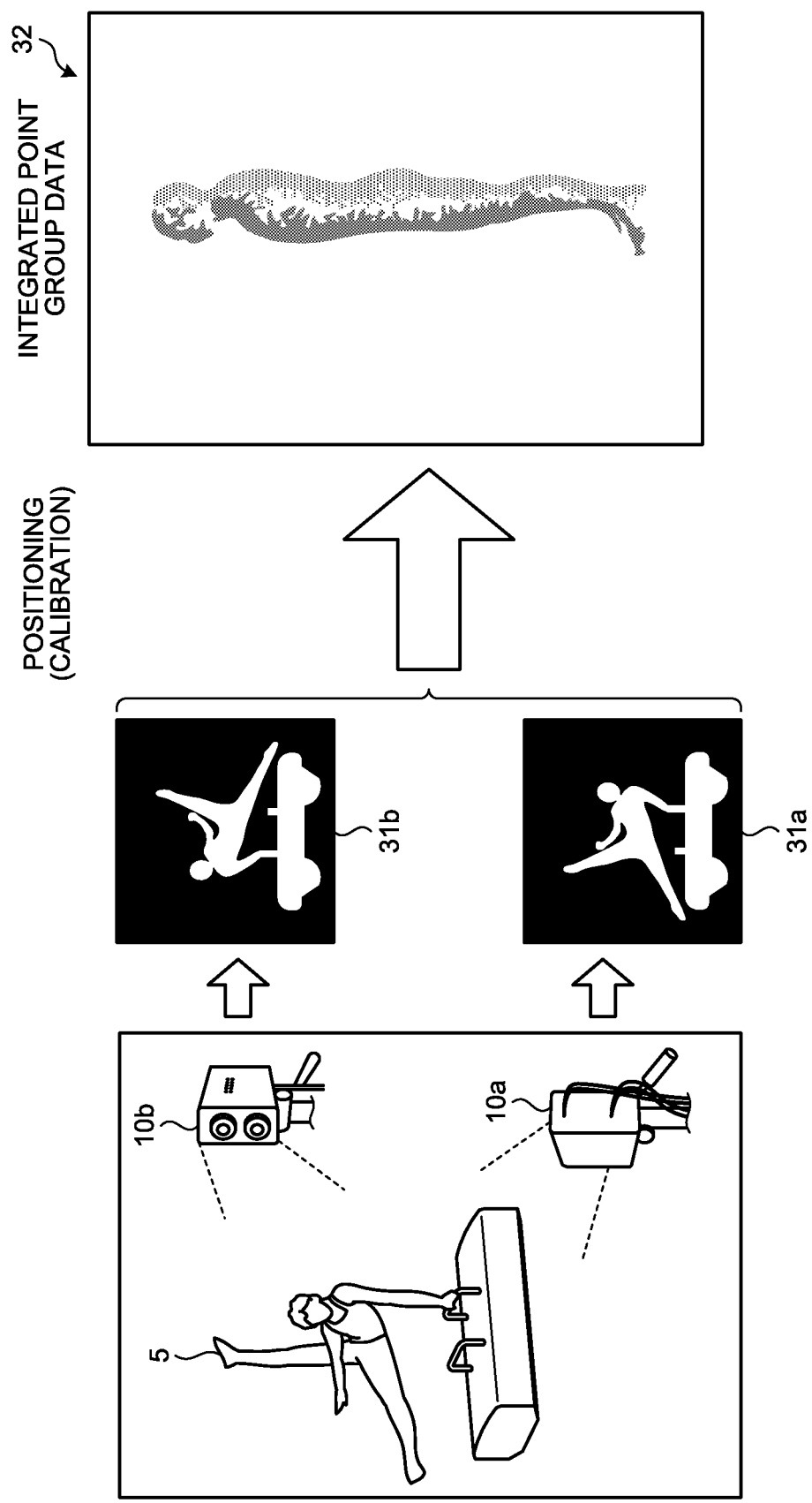
FIG. 11 is a diagram illustrating exemplary integration of point group data of a plurality of distance sensors.
Figure 12:
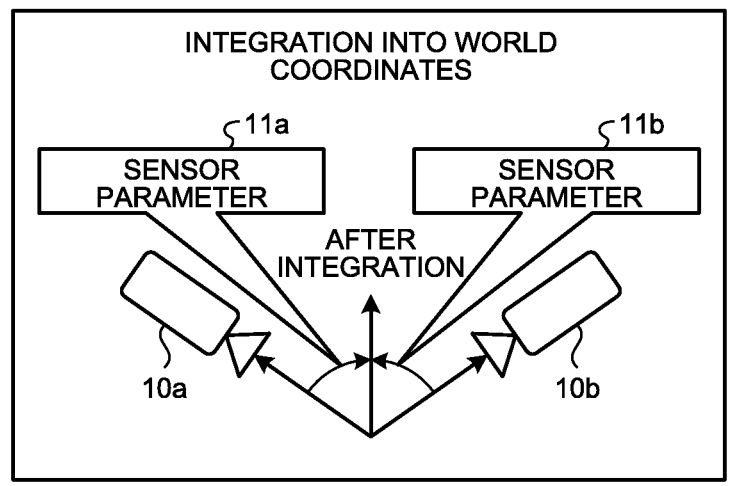
FIG. 12 is a diagram illustrating exemplary integration of the coordinates of each distance sensor with the world coordinates.
Figure 13:
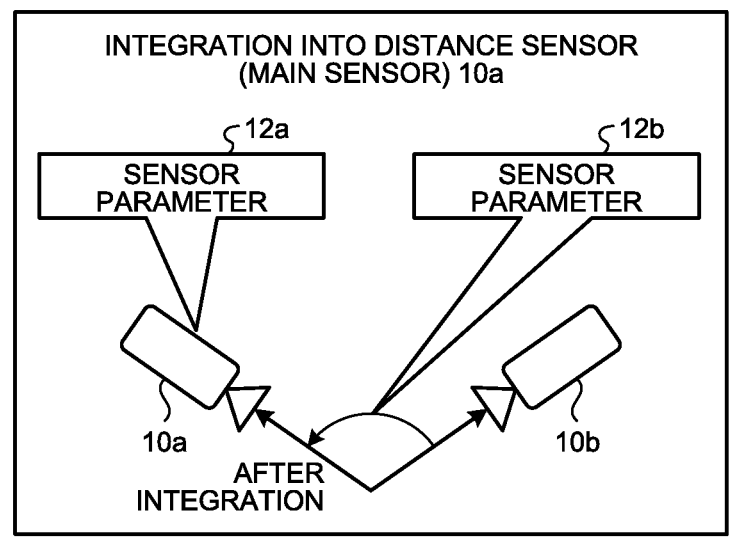
FIG. 13 is a diagram illustrating exemplary integration of the coordinates of each distance sensor with the coordinates of a main sensor.

The following describes the integration of the point group data with reference to FIGS. 11 to 13. FIG. 11 is a diagram illustrating exemplary integration of the point group data of a plurality of distance sensors. As illustrated in FIG. 11, the calculation unit 132 generates pieces of the point group data based on respective distance images 31a and 31b as outputs from the main sensor 10a and the sub sensor 10b that measure the person 5. The calculation unit 132 integrates the generated pieces of the point group data into, for example, the coordinates of the main sensor 10a, thereby generating integrated point group data 32.

At the time of integrating the point group data, the calculation unit 132 performs positioning of each point group data with the integrated coordinates. The calculation unit 132 determines, through calibration, sensor parameters and affine transform matrices for converting the coordinates of each distance sensor 10. The calibration is performed by using an instrument selected for the calibration or a general-purpose calibration jig.

The positioning sensor parameters are θxrot representing the rotation angle about the x axis, θyrot representing the rotation angle about the y axis, θzrot representing the rotation angle about the z axis, $t_x$ representing translation along the x axis, $t_y$ representing translation along the y axis, and $t_z$ representing translation along the z axis. The affine transform matrices are Expressions (1) to (4) described below. Expression (1) expresses rotation about the x axis with θ=θxrot. Expression (2) expresses rotation about the y axis with θ=θyrot. Expression (3) expresses rotation about the z axis with θ=θzrot. Expression (4) expresses translation.

[Mathematical 1]

... (1)

[Mathematical 2]

... (2)

[Mathematical 3]

... (3)

[Mathematical 4]

... (4)

FIG. 12 is a diagram illustrating an example in which the coordinates of each distance sensor are integrated into the world coordinates. In the example in FIG. 12, the calculation unit 132 integrates the coordinates of the main sensor 10a and the coordinates of the sub sensor 10b into the world coordinates by using sensor parameters 11a and 11b, respectively.

FIG. 13 is a diagram illustrating an example in which the coordinates of each distance sensor are integrated into the coordinates of the main sensor. In the example in FIG. 13, the calculation unit 132 integrates the coordinates of the main sensor 10a and the coordinates of the sub sensor 10b into the coordinates of the main sensor 10a by using sensor parameters 12a and 12b, respectively. In this case, all sensor parameters 12a corresponding to the main sensor 10a become zero.

Subsequently, the calculation unit 132 generates inverted affine transform matrices for returning to the original position of each distance sensor 10 from each sensor parameter obtained through the calibration and corresponding to the integrated point group data. In this case, θ is −θxrot for the x axis, θ is −θyrot for the y axis, and θ is −θzrot for the z axis.

The calculation unit 132 calculates a converted vector for each distance sensor 10 by multiplying a unit vector, for example, the z-directional unit vector by the inverted affine transform matrix. The calculation unit 132 acquires the spin-direction angle by projecting each converted vector corresponding to each distance sensor 10 onto the xz plane. Accordingly, the calculation unit 132 determines the installation position of each distance sensor 10 on the plane.

In addition, the calculation unit 132 acquires the handstand-direction angle by projecting the converted vector corresponding to each distance sensor 10 onto the yz plane. In other words, the calculation unit 132 determines the relative height and elevation of each distance sensor 10. In this example, it is assumed for simplification that the relative height and elevation are set to be equal between the distance sensors 10 and the vectors corresponding to the respective distance sensors 10 are substantially same. The calculation unit 132 stores the spin-direction angle and the handstand-direction angle thus acquired in the positional relation storage unit 121. Having stored the spin-direction angle and the handstand-direction angle in the positional relation storage unit 121, the calculation unit 132 outputs a combination determination instruction to the first determination unit 133.

Figure 14:
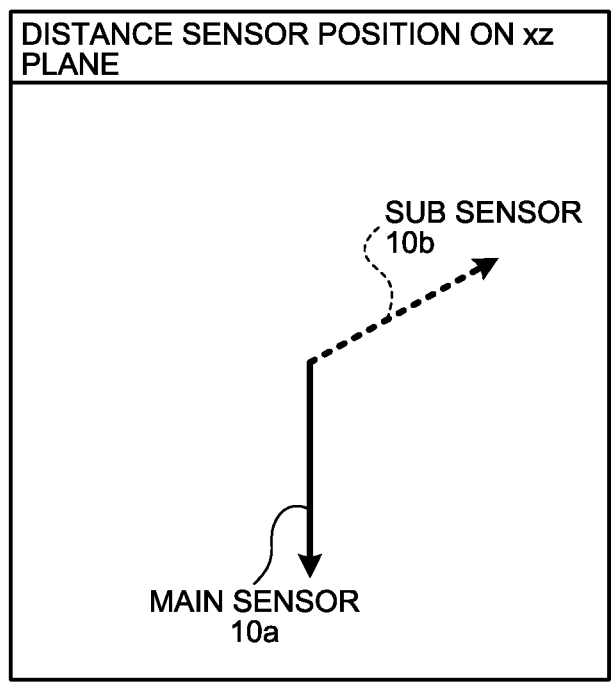
FIG. 14 is a diagram illustrating an exemplary position of each distance sensor on an xz plane.
Figure 15:
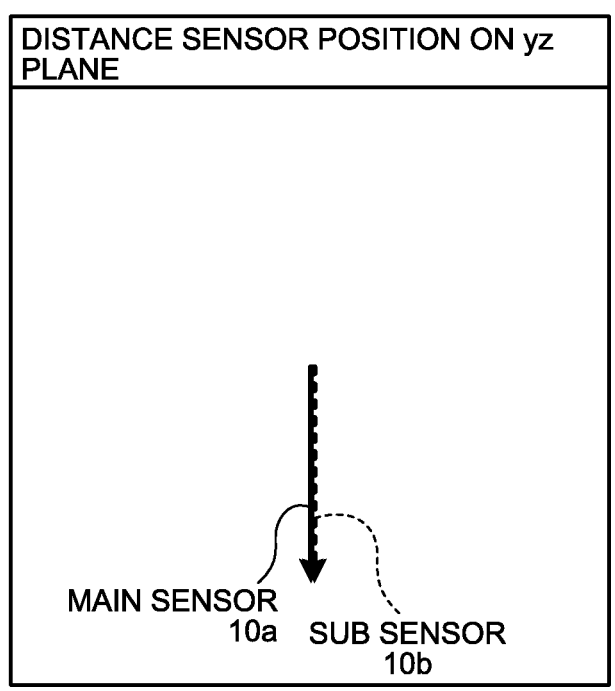
FIG. 15 is a diagram illustrating an exemplary position of each distance sensor on a yz plane.

The following describes the vector corresponding to the position of each distance sensor 10 with reference to FIGS. 14 and 15. FIG. 14 is a diagram illustrating an exemplary position of each distance sensor on the xz plane. In the example in FIG. 14, the vectors corresponding to the main sensor 10a and the sub sensor 10b have directions upon reflection of sensor disposition. FIG. 15 is a diagram illustrating an exemplary position of each distance sensor on the yz plane. As described above, in the example in FIG. 15, the vectors corresponding to the main sensor 10a and the sub sensor 10b have substantially same directions.

In FIG. 8, when the combination determination instruction is input from the calculation unit 132, the first determination unit 133 refers to the positional relation storage unit 121 and acquires the spin-direction and handstand-direction angles of each distance sensor 10. The first determination unit 133 determines the angle between the distance sensors 10, in other words, the angle between the vectors corresponding to the respective distance sensor 10 based on the acquired handstand-direction and spin-direction angles of each distance sensor 10.

The first determination unit 133 determines all combinations of posture numbers for each of the spin and handstand directions based on the angle between the distance sensors 10. The first determination unit 133 stores the determined combinations in the combination storage unit 122.

Figure 16:
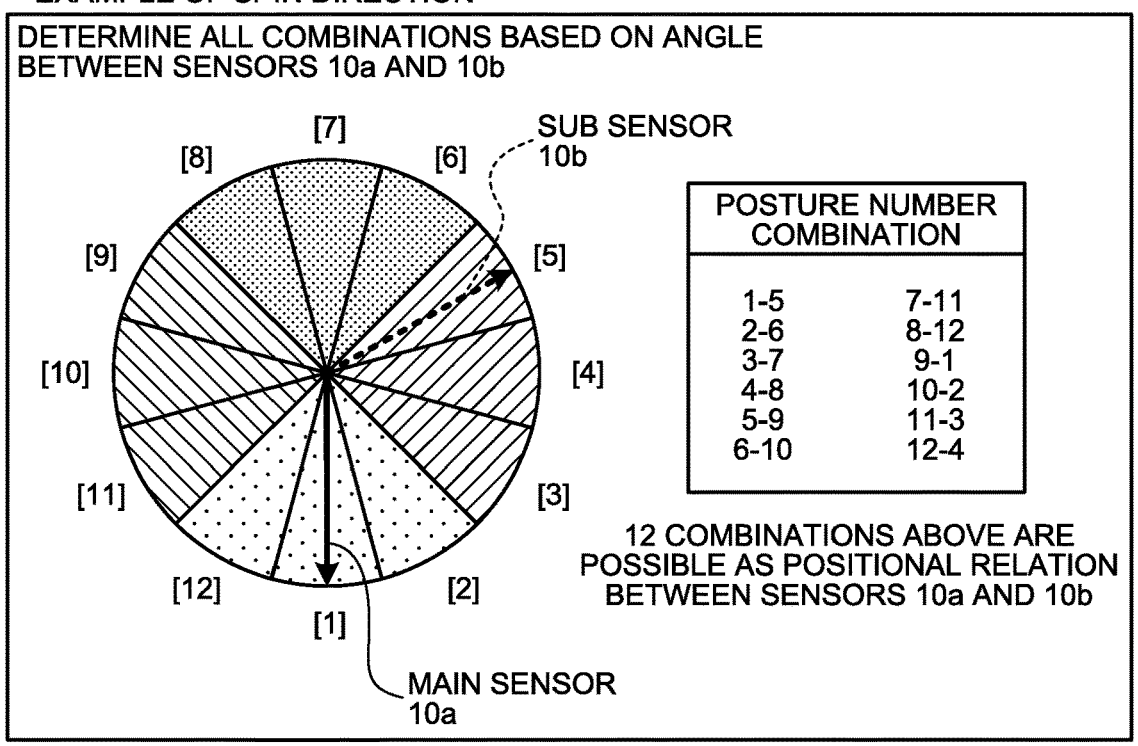
FIG. 16 is a diagram illustrating all exemplary combinations of posture numbers in a spin direction.
Figure 17:
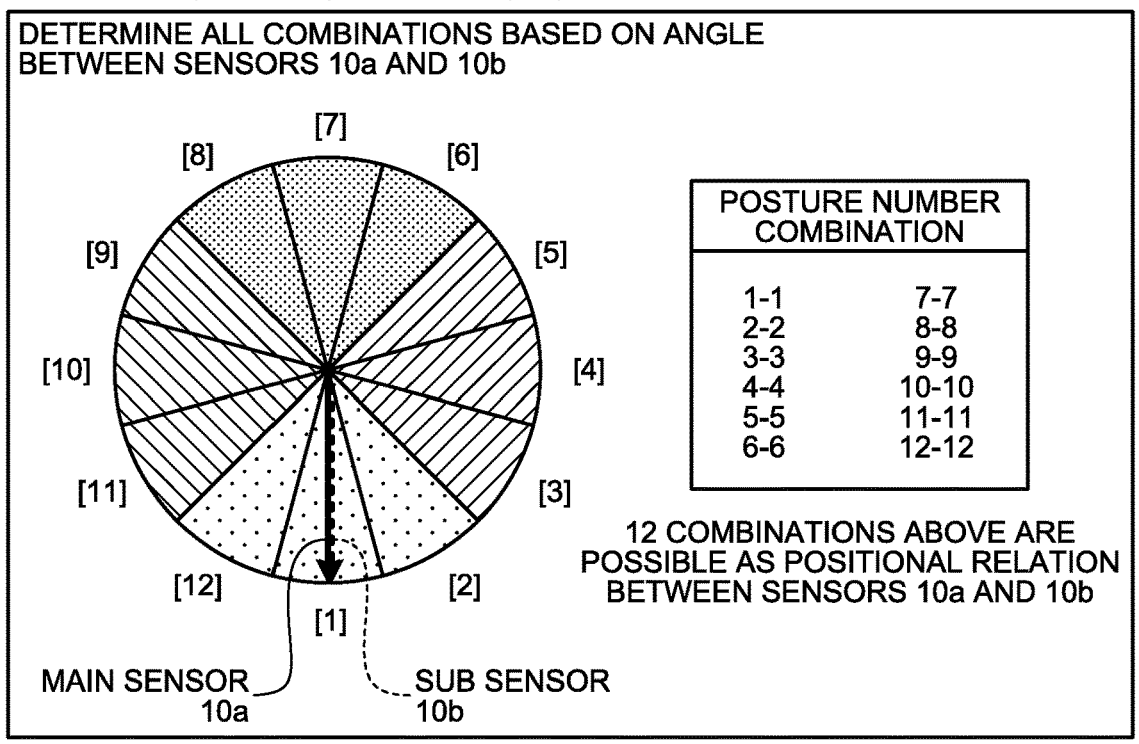
FIG. 17 is a diagram illustrating all exemplary combinations of posture numbers in a handstand direction.

FIGS. 16 and 17 illustrate an example of determined combinations. FIG. 16 is a diagram illustrating all exemplary combinations of posture numbers in the spin direction. In the example in FIG. 16, 12 combinations of "1-5", "2-6", "3-7", . . . are determined as all combinations of posture numbers corresponding to the angle between the main sensor 10a and the sub sensor 10b. The 12 combinations are possible as the positional relation between the main sensor 10a and the sub sensor 10b.

FIG. 17 is a diagram illustrating all exemplary combinations posture numbers in the handstand direction. In the example in FIG. 17, 12 combinations of "1-1", "2-2", "3-3", . . . are determined as all combinations of posture numbers corresponding to the angle between the main sensor 10a and the sub sensor 10b. The 12 combinations are possible as the positional relation between the main sensor 10a and the sub sensor 10b. The first determination unit 133 determines combinations in the same manner when the number of distance sensors 10 is three or larger.

In this manner, the calculation unit 132 and the first determination unit 133 are each an exemplary acquisition unit that acquires the positional relation between the distance sensors 10 each of which senses (measures) the distance to the person 5 as an object. The acquisition unit in this case may include the acquisition unit 131 that acquires the distance image from each distance sensor 10.

In FIG. 8, the distance image corresponding to each distance sensor 10 is input from the acquisition unit 131 to the posture recognition unit 134. The posture recognition unit 134 refers to the posture recognition dictionary storage unit 123 and executes the posture recognition for each distance sensor 10 based on the distance image of the distance sensor 10. The posture recognition unit 134 calculates, for each combination of posture numbers in the spin and handstand directions, the probability of the orientation (posture) of the object as a result of the posture recognition. The posture recognition unit 134 uses, for example, 15 combinations having highest probabilities in 144 combinations since the number of posture numbers in the spin and handstand directions is 12 for each distance sensor 10. The combinations of posture numbers in the spin and handstand directions, the probabilities of which are to be used are not limited to highest 15 combinations but may be combinations in an optional number.

The posture recognition unit 134 calculates, for each of the spin and handstand directions, the likelihood of each combination of the posture numbers of the distance sensors 10 by referring to the combination storage unit 122 and summing the probabilities of the orientation of the object for the combination of the posture numbers of the distance sensors 10. The posture recognition unit 134 calculates the likelihood of Combination "2-6" to be "0.7", for example, when the probability of Posture number "2" of the main sensor 10a for Combination "2-6" is "0.3" and the probability of Posture number "6" of the sub sensor 10b for Combination "2-6" is "0.4". The posture recognition unit 134 calculates the likelihood of each combination and determines posture numbers of the distance sensors 10 of a combination, the likelihood of which is maximum. The posture recognition unit 134 determines the determined posture numbers to be dictionary numbers of the distance sensors 10. Each dictionary number corresponds to a posture number in the skeleton recognition dictionary storage unit 124 and specifies a skeleton recognition dictionary used to estimate the three-dimensional position of the skeleton of the object. The posture recognition unit 134 outputs the determined spin-direction and handstand-direction dictionary numbers of each distance sensor 10 to the estimation unit 135.

Figure 18:
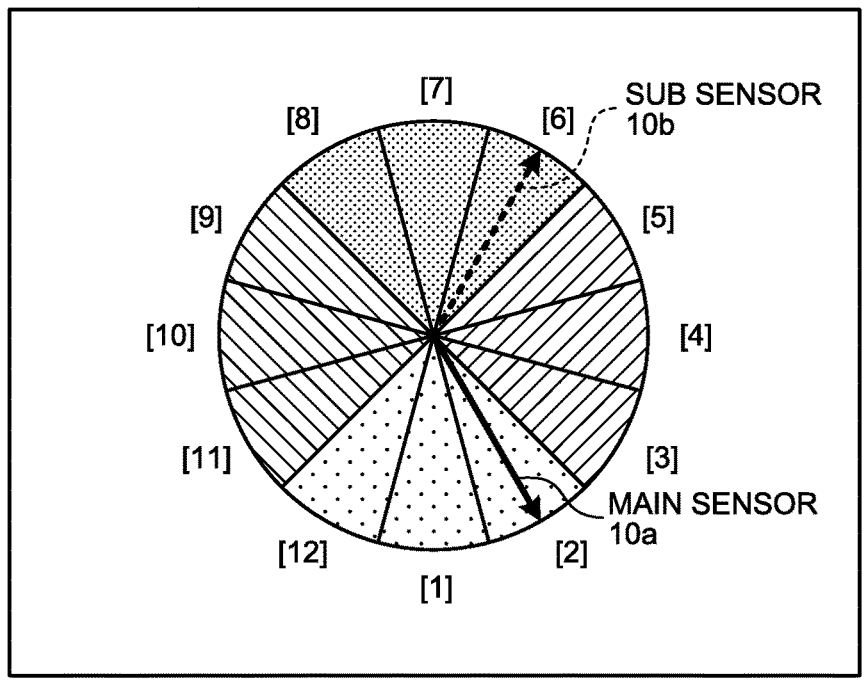
FIG. 18 is a diagram illustrating exemplary dictionary number determination in the spin direction.

FIG. 18 is a diagram illustrating exemplary dictionary number determination in the spin direction. For example, when the likelihood "0.7" of Combination "2-6" is maximum in the spin direction as illustrated in FIG. 18, the dictionary number of the main sensor 10a is determined to be Posture number "2", and the dictionary number of the sub sensor 10b is determined to be Posture number "6".

Figure 19:
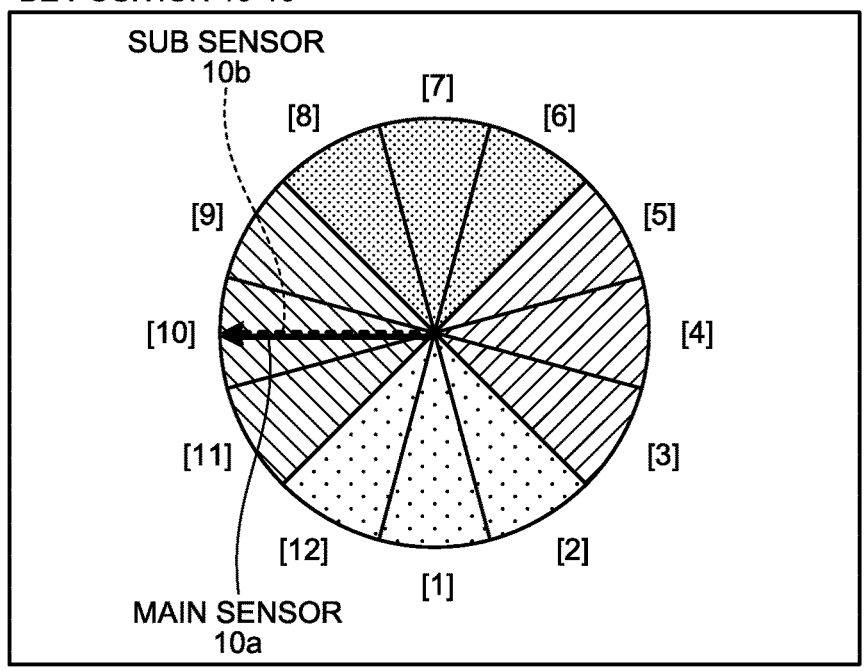
FIG. 19 is a diagram illustrating exemplary dictionary number determination in the handstand direction.

FIG. 19 is a diagram illustrating exemplary dictionary number determination in the handstand direction. For example, when the likelihood "0.8" of Combination "10-10" is maximum in the handstand direction as illustrated in FIG. 19, the dictionary amount of the main sensor 10a and the sub sensor 10b are determined to be Posture number "10".

Figure 20:
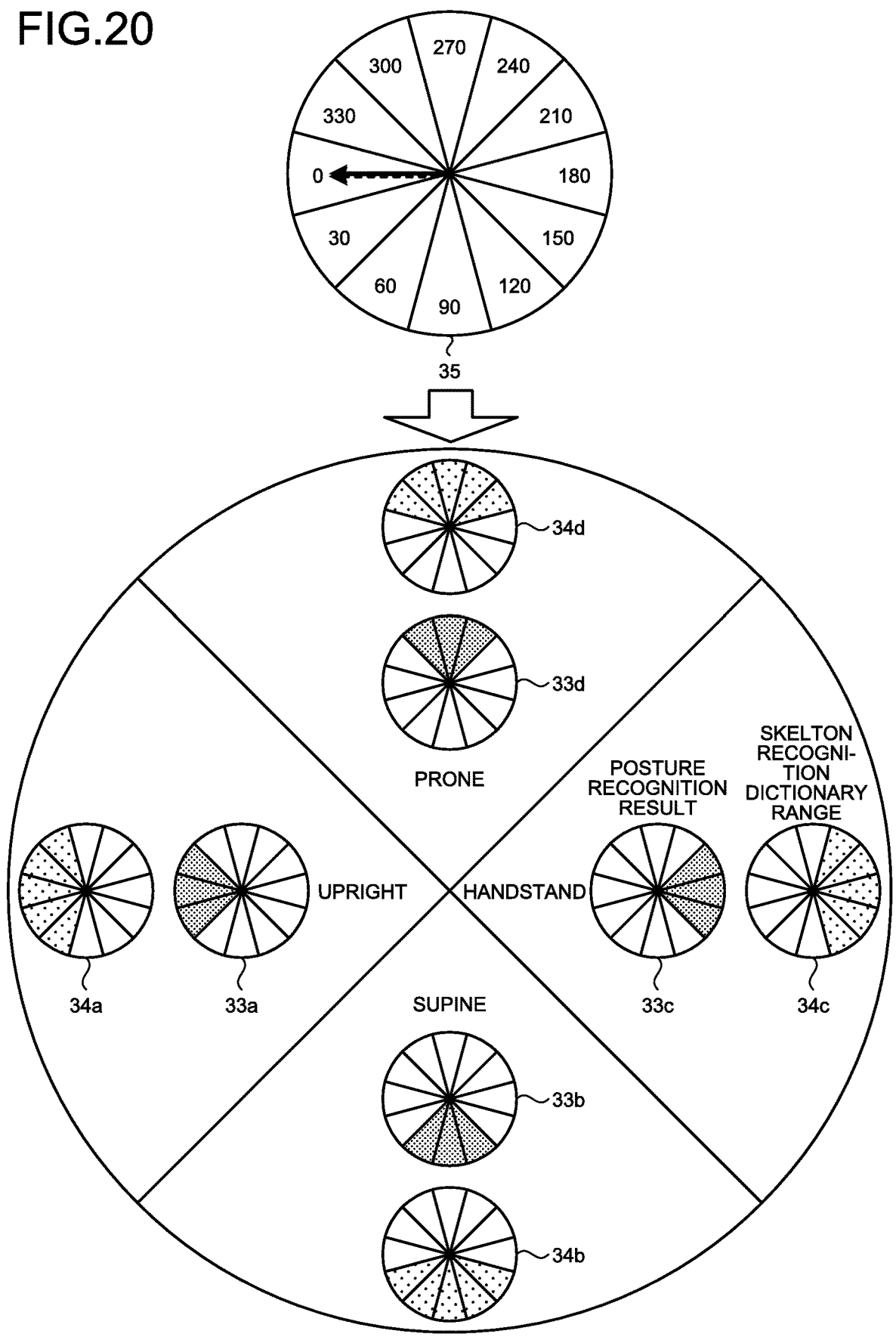
FIG. 20 is a diagram illustrating an exemplary posture recognition result in the handstand direction and an exemplary skeleton recognition dictionary selection range.
Figure 21:
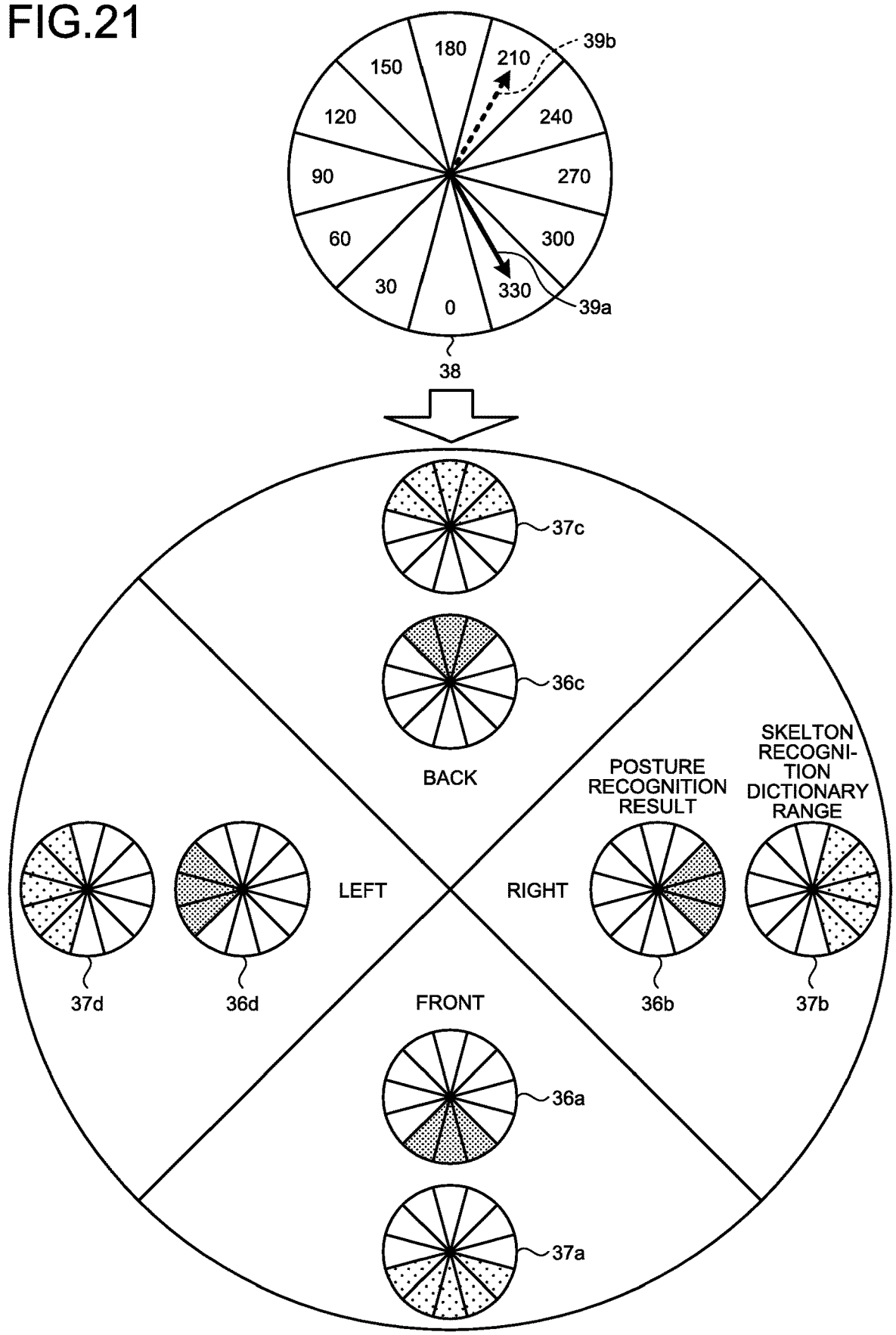
FIG. 21 is a diagram illustrating an exemplary posture recognition result in the spin direction and an exemplary skeleton recognition dictionary selection range.

The following describes a posture recognition result and a skeleton recognition dictionary selection range with reference to FIGS. 20 and 21. FIG. 20 is a diagram illustrating an exemplary posture recognition result in the handstand direction and an exemplary skeleton recognition dictionary selection range. As illustrated in FIG. 20, the posture recognition result in the handstand direction is classified into four directions of upright, prone, handstand, and supine. For each of the four directions, the skeleton recognition dictionary selection range is increased by one posture number in each of directions expanding from the posture recognition result. Specifically, a skeleton recognition dictionary range 34a corresponds to a posture recognition result 33a for upright, and a skeleton recognition dictionary range 34b corresponds to a posture recognition result 33b for prone. In addition, a skeleton recognition dictionary range 34c corresponds to a posture recognition result 33c for handstand, and a skeleton recognition dictionary range 34d corresponds to a posture recognition result 33d for supine. The increase of each skeleton recognition dictionary range as compared to the corresponding posture recognition result is preparation for error in the posture recognition. In an exemplary posture recognition result illustrated in a circle 35, the vectors corresponding to the main sensor 10a and the sub sensor 10b point to the direction of 0°, in other words, Posture number "1". In this case, the posture recognition result is "upright", and the skeleton recognition dictionary range is "upright".

FIG. 21 is a diagram illustrating an exemplary the posture recognition result and an exemplary skeleton recognition dictionary selection range in the spin direction. As illustrated in FIG. 21, the posture recognition result in the spin direction is classified into four directions of front, right, back, and left. For each of the four directions, the skeleton recognition dictionary selection range is increased by one posture number in each of directions expanding from the posture recognition result. Specifically, a skeleton recognition dictionary range 37a corresponds to a posture recognition result 36a for front, and a skeleton recognition dictionary range 37b corresponds to a posture recognition result 36b for right. In addition, a skeleton recognition dictionary range 37c corresponds to a posture recognition result 36c for back, and a skeleton recognition dictionary range 37d corresponds to a posture recognition result 36d for left. The increase of each skeleton recognition dictionary range as compared to the posture recognition result is preparation for error in the posture recognition.

In an exemplary posture recognition result illustrated in a circle 38, a vector 39a corresponding to the main sensor 10a points to the direction of 330°, in other words, Posture number "2". In this case, the posture recognition result is "front", and the skeleton recognition dictionary range is "front". In addition, a vector 39b corresponding to the sub sensor 10b points to the direction of 210°, in other words, Posture number "6". In this case, the posture recognition result is "back", and the skeleton recognition dictionary range is "back".

In this manner, the posture recognition unit 134 provisionally classifies the orientation of the object relative to each individual distance sensor 10 included in the distance sensors 10 into one of a plurality of classifications based on sensing data acquired by the individual distance sensor 10. The classifications correspond to posture numbers. The posture recognition unit 134 calculates the likelihood of each combination corresponding to the positional relation between the distance sensors 10 based on a result (posture number) of the provisional classification of the orientation of the object relative to each individual distance sensor 10. The posture recognition unit 134 classifies the orientation of the object corresponding to each individual distance sensor 10 in accordance with the calculated likelihood of each combination. The classified orientation of the object is a dictionary number corresponding to a posture number. Accordingly, the posture recognition unit 134 is an exemplary first classification unit that provisionally classifies the orientation of the object, an exemplary calculation unit that calculates the likelihood of each combination, and an exemplary second classification unit that classifies the orientation of the object corresponding to each distance sensor 10 in accordance with the likelihood of each combination.

The posture recognition unit 134 calculates the likelihood of each combination corresponding to the positional relation between the distance sensors 10 in the direction in which the object handstands and the direction in which the object spins. In addition, the posture recognition unit 134 classifies the orientation of the object corresponding to each individual distance sensor 10 in accordance with likelihood as the sum of the likelihood of each individual distance sensor 10 corresponding to the combination.

In FIG. 8, the estimation unit 135 receives inputting of the distance image from the acquisition unit 131 and inputting of the dictionary numbers of each distance sensor 10 in the spin and handstand directions from the posture recognition unit 134. The estimation unit 135 refers to the skeleton recognition dictionary storage unit 124 and generates a site label image by using the skeleton recognition dictionary based on the distance image and dictionary numbers of each distance sensor 10. The site label image is an image in which a site of the person 5 as an object is labeled based on the distance (depth).

The estimation unit 135 extracts boundary pixels of each joint site from the generated site label image. The estimation unit 135 converts pixels corresponding to boundary pixels of the distance image of each distance sensor 10 into a point group based on the extracted boundary pixels of each joint site, and extracts the boundary point group of each joint site. The estimation unit 135 outputs the extracted boundary point group of each joint site for each distance sensor 10 to the second determination unit 136.

In other words, the estimation unit 135 acquires sensing data acquired by each individual distance sensor 10 included in the distance sensors 10. The estimation unit 135 estimates the three-dimensional position of the skeleton of the object when viewed from each individual distance sensor 10 based on each acquired sensing data and the skeleton recognition dictionary selected in accordance with the orientation of the object relative to the individual distance sensor 10. Alternatively, the estimation unit 135 generates a site label image in which a site of the object is expressed by a site label by using the skeleton recognition dictionary based on the sensing data, and estimates the three-dimensional position of the skeleton of the object based on the site label in the generated site label image. Alternatively, the estimation unit 135 estimates the three-dimensional position of the skeleton of the object by using data of the vicinity of the boundary of the site label in the sensing data.

The estimation unit 135 may output, to the second determination unit 136, a boundary point group obtained by calculating dispersion of the boundary point group of each joint site corresponding to each distance sensor 10 and randomly thinning or increasing the boundary point group by using the reciprocal of the calculated dispersion. Specifically, the estimation unit 135 calculates dispersion of data of the vicinity of the boundary for each individual distance sensor 10. The estimation unit 135 estimates the three-dimensional position of the skeleton of the object by using sensing data obtained by randomly thinning or increasing the sensing data of each individual distance sensor 10 by using the reciprocal of the calculated dispersion.

Figure 22:
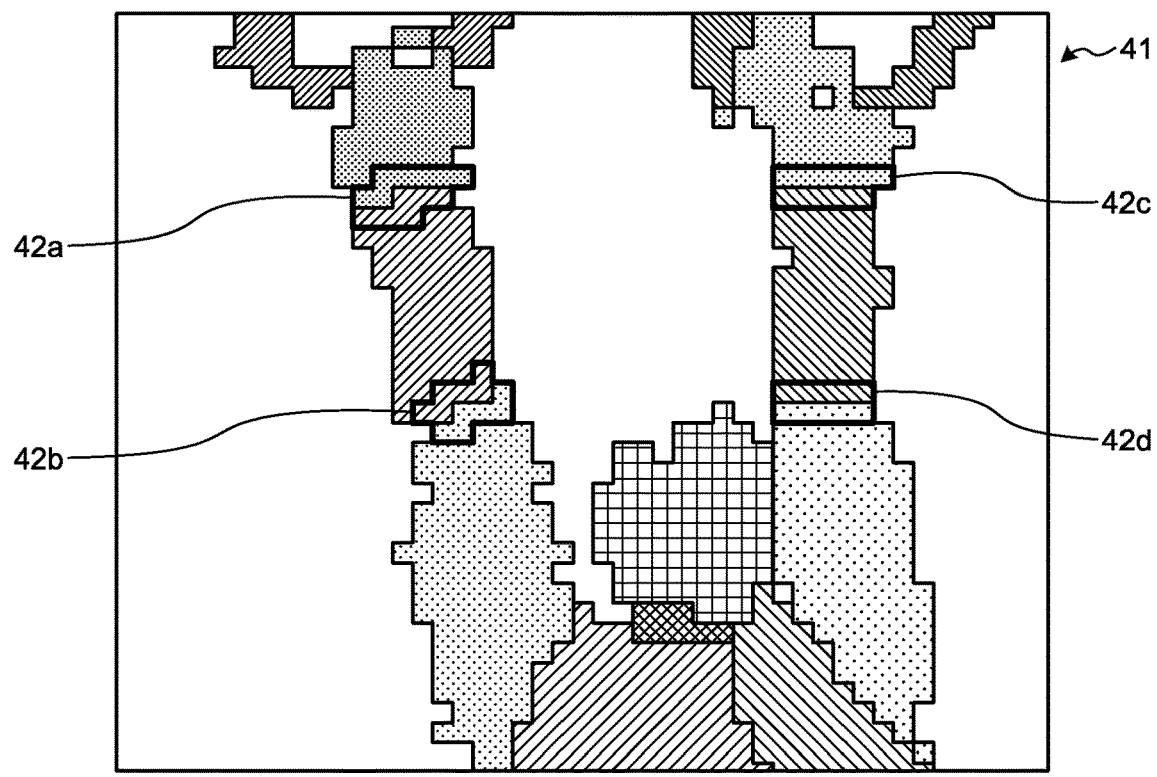
FIG. 22 is a diagram illustrating exemplary boundary pixels in a site label image.
Figure 23:
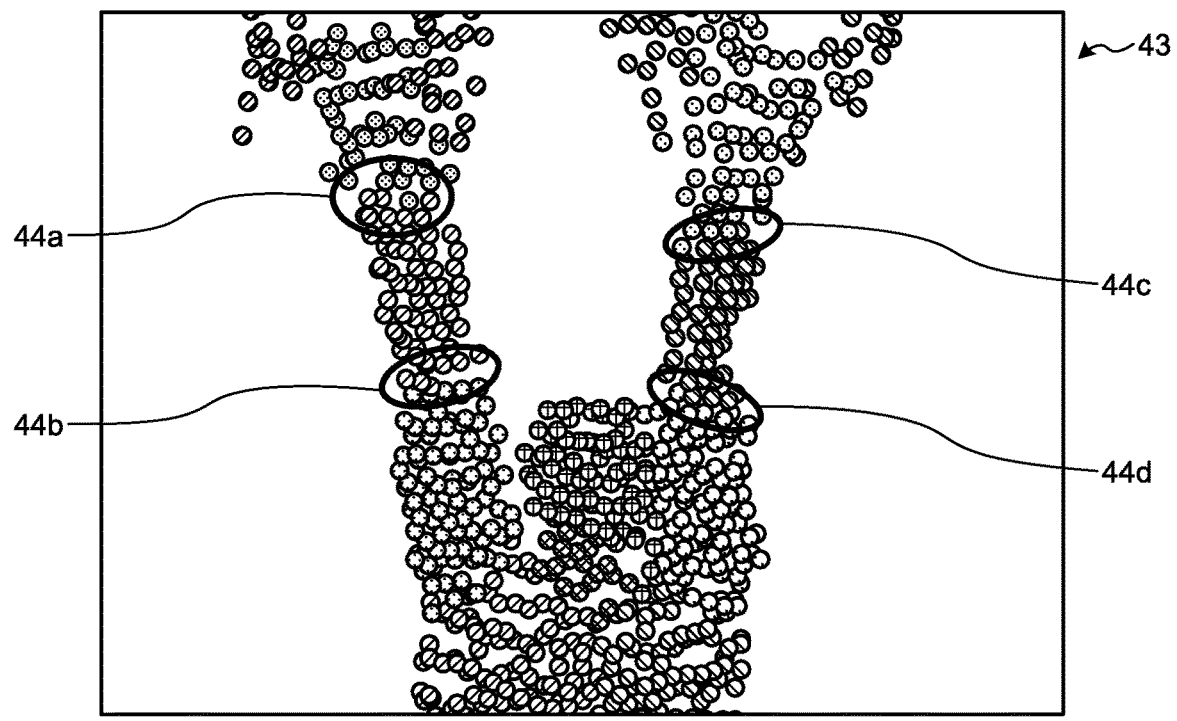
FIG. 23 is a diagram illustrating an exemplary boundary point group of each joint site.

The following describes the boundary point group of each joint site with reference to FIGS. 22 and 23. FIG. 22 is a diagram illustrating exemplary boundary pixels in a site label image. In this site label image 41 illustrated in FIG. 22, each pixel at the boundary of a site label is extracted as a boundary pixel of a joint site. Boundary pixels 42a and 42b correspond to the right wrist and the right elbow, respectively. Boundary pixels 42c and 42d correspond to the left wrist and the left elbow, respectively.

FIG. 23 is a diagram illustrating an exemplary boundary point group of each joint site. Point group data 43 illustrated in FIG. 23 is obtained by converting the distance image corresponding to the site label image 41 into the three coordinate axes of the x, y, and z axes. In the point group data 43, a point group corresponding to the extracted boundary pixels of each joint site in FIG. 22 is extracted as the boundary point group of the joint site. Boundary point groups 44a and 44b correspond to the boundary pixels 42a and 42b and correspond to the right wrist and the right elbow, respectively. Boundary point groups 44c and 44d correspond to the boundary pixels 42c and 42d and correspond to the left wrist and the left elbow, respectively.

In FIG. 8, the extracted boundary point group of each joint site of each distance sensor 10 is input from the estimation unit 135 to the second determination unit 136. The second determination unit 136 refers to the positional relation storage unit 121 and integrates the extracted boundary point group of each joint site of each distance sensor 10 into the coordinates of the main sensor 10a by using sensor parameters. The second determination unit 136 may use the world coordinates as the coordinates into which the integration is performed.

The second determination unit 136 calculates the barycenter of the integrated boundary point group of each joint site and determines the coordinates of the barycenter to be joint coordinates. In other words, the second determination unit 136 determines the three-dimensional position of the skeleton of the person 5 as an object. The second determination unit 136 outputs the determined joint coordinates to, for example, a processing unit or processing device that performs fitting to the distance image. For example, the second determination unit 136 may output the determined joint coordinates to, for example, a processing unit or processing device that performs gymnastics scoring or may output the determined joint coordinates as a skeleton model usable for computer graphics (CG) animation. In addition, the second determination unit 136 may fabricate the determined joint coordinates into, for example, a particular format and output the joint coordinates to an external storage device (not illustrated) or the like. The second determination unit 136 may generate a three-dimensional model based on the determined joint coordinates, output the three-dimensional model to the display unit 111, and display the three-dimensional model.

In other words, the second determination unit 136 determines the three-dimensional position of the skeleton of the object based on a result of estimation of the three-dimensional position of the skeleton of the object when viewed from each individual distance sensor 10 and the positional relation between the distance sensors 10. In addition, the second determination unit 136 determines the barycenter of the boundaries of site labels to be a joint position.

The second determination unit 136 may calculate the barycenter for the boundary point group of each joint site corresponding to the distance sensor 10 that has the shortest distance to the person 5 as an object. Specifically, the second determination unit 136 may calculate the barycenter of the boundaries by using a result of estimation of the three-dimensional position of the skeleton when viewed from the distance sensor 10, the distance of which to the object is shortest among the distance sensors 10. The second determination unit 136 may determine, for example, the position (coordinates) of a site such as the center between both shoulders or the crotch based on a plurality of determined joint positions (joint coordinates). For the head, the toes, and the like, the second determination unit 136 may determine the centroid of a site label to be the position (coordinates) of a site corresponding to the site label.

Figure 24:
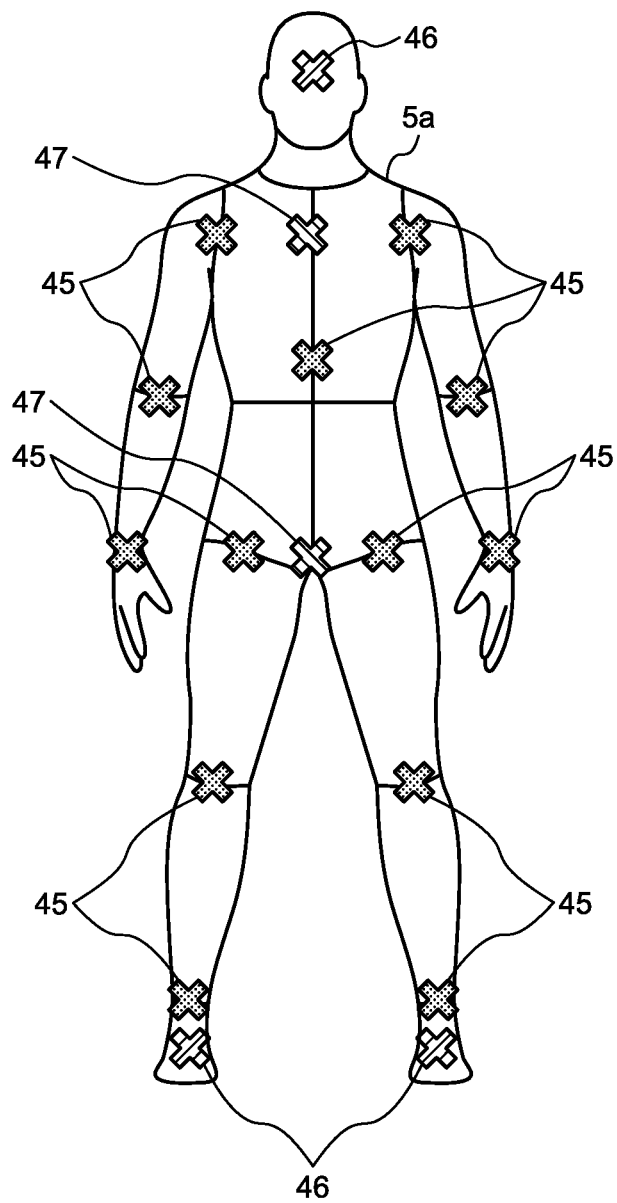
FIG. 24 is a diagram illustrating exemplary joint coordinates.
Figure 25:
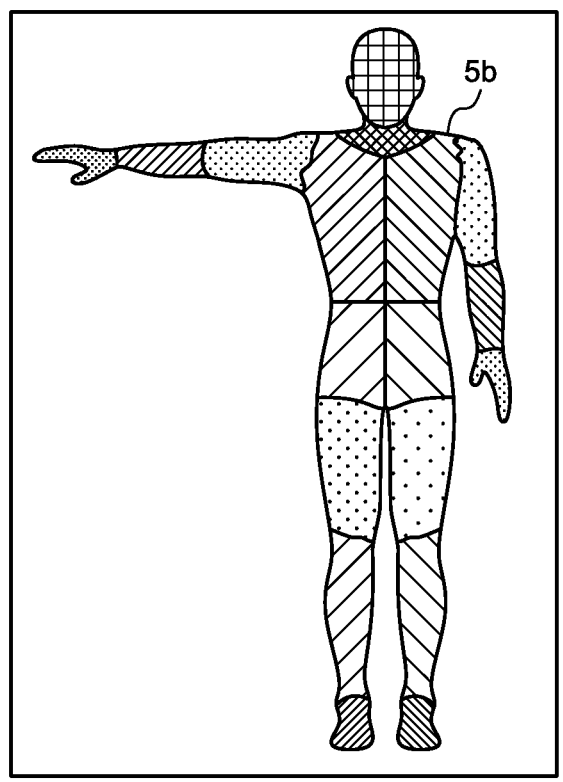
FIG. 25 is a diagram illustrating an exemplary site label image.

The following describes joint coordinates and a site label with reference to FIGS. 24 and 25. FIG. 24 is a diagram illustrating exemplary joint coordinates. FIG. 24 illustrates a state in which labeling is performed on a person 5a, and each joint position expressed by joint coordinates 45, each site expressed by a centroid 46 of a site label, and position 47 of each site based on a plurality of joint coordinates 45 are determined.

FIG. 25 is a diagram illustrating an exemplary site label image. The site label image of a person 5b illustrated in FIG. 25 is the site label image corresponding to the labeling of the person 5a illustrated in FIG. 24. The persons 5a and 5b are identical to each other although the position of the right hand is different between the persons.

The following describes operation of the recognition device 100 according to the embodiment. The description is first made on the first recognition processing of performing the posture recognition with reference to FIGS. 26 to 30.

Figure 26:
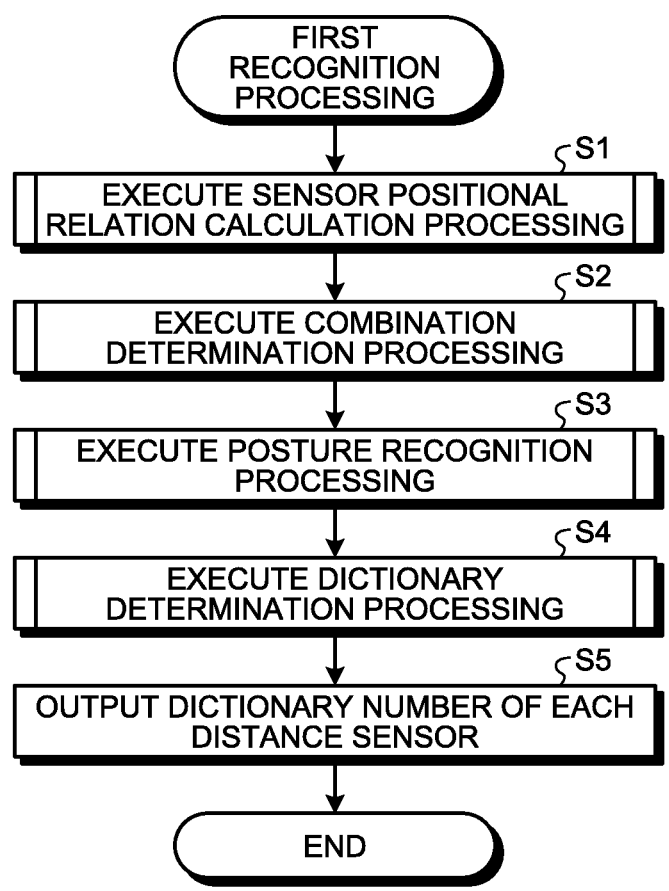
FIG. 26 is a flowchart illustrating exemplary first recognition processing according to the embodiment.

FIG. 26 is a flowchart illustrating exemplary the first recognition processing according to the embodiment.

The acquisition unit 131 of the recognition device 100 receives and acquires the distance image from each distance sensor 10. The acquisition unit 131 outputs the acquired distance image to the calculation unit 132, the posture recognition unit 134, and the estimation unit 135. When the distance image is input from the acquisition unit 131, the calculation unit 132 executes sensor positional relation calculation processing (step S1).

Figure 27:
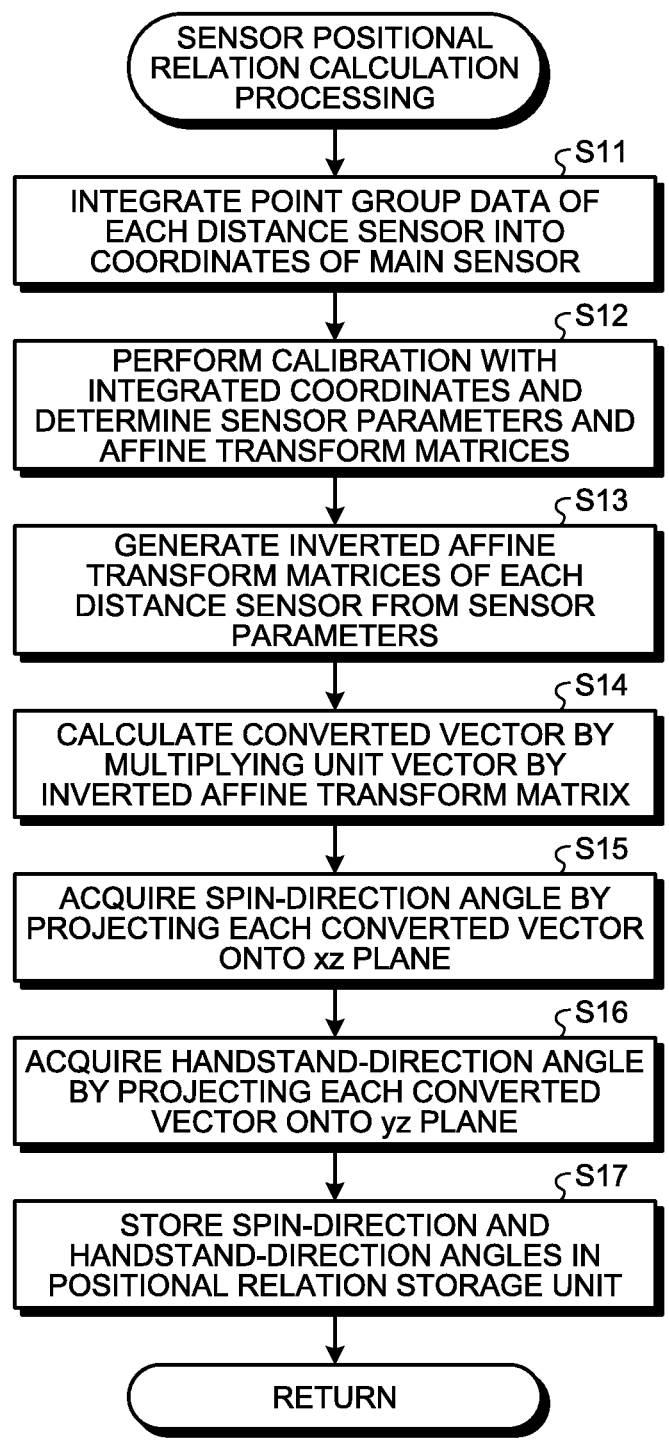
FIG. 27 is a flowchart illustrating exemplary sensor positional relation calculation processing.

The following describes the sensor positional relation calculation processing with reference to FIG. 27. FIG. 27 is a flowchart illustrating exemplary sensor positional relation calculation processing.

When the distance image is input from the acquisition unit 131, the calculation unit 132 converts the distance image of each distance sensor 10 into the point group data. The calculation unit 132 integrates the converted point group data of each distance sensor 10 into the coordinates of the main sensor 10a (step S11).

The calculation unit 132 calibrates each point group data with the integrated coordinates. The calculation unit 132 determines sensor parameters and affine transform matrices of each distance sensor 10 through the calibration (step S12).

The calculation unit 132 generates inverted affine transform matrices of each distance sensor 10 from the sensor parameters (step S13). The calculation unit 132 calculates the converted vector of each distance sensor 10 by multiplying a unit vector by the corresponding inverted affine transform matrix (step S14).

The calculation unit 132 acquires the spin-direction angle by projecting each converted vector corresponding to each distance sensor 10 onto the xz plane (step S15). In addition, the calculation unit 132 acquires the handstand-direction angle by projecting the converted vector corresponding to each distance sensor 10 onto the yz plane (step S16). The calculation unit 132 stores the acquired spin-direction and handstand-direction angles in the positional relation storage unit 121 (step S17), outputs a combination determination instruction to the first determination unit 133, and then returns to the original processing. Accordingly, the calculation unit 132 can calculate the positional relation between the distance sensors 10.

In FIG. 26, when the combination determination instruction is input from the calculation unit 132, the first determination unit 133 executes combination determination processing (step S2).

Figure 28:
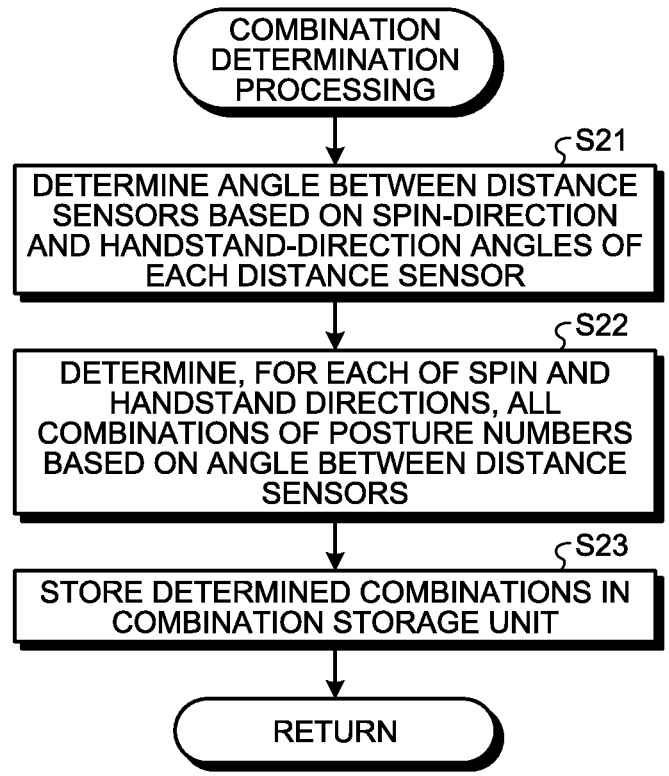
FIG. 28 is a flowchart illustrating exemplary combination determination processing.

The following describes the combination determination processing with reference to FIG. 28. FIG. 28 is a flowchart illustrating exemplary combination determination processing.

The first determination unit 133 refers to the positional relation storage unit 121 and acquires the spin-direction and handstand-direction angles of each distance sensor 10. The first determination unit 133 determines the angle between the distance sensors 10 based on the acquired spin-direction and handstand-direction angles of each distance sensor 10 (step S21).

The first determination unit 133 determines, for each of the spin and handstand directions, all combinations of posture numbers based on the angle between the distance sensors 10 (step S22). The first determination unit 133 stores the determined combinations in the combination storage unit 122 (step S23), and returns to the original processing. Accordingly, the first determination unit 133 can determine combinations of posture numbers based on the angle between the distance sensors 10.

In FIG. 26, when the distance image corresponding to each distance sensor 10 is input from the acquisition unit 131, the posture recognition unit 134 executes posture recognition processing (step S3).

Figure 29:
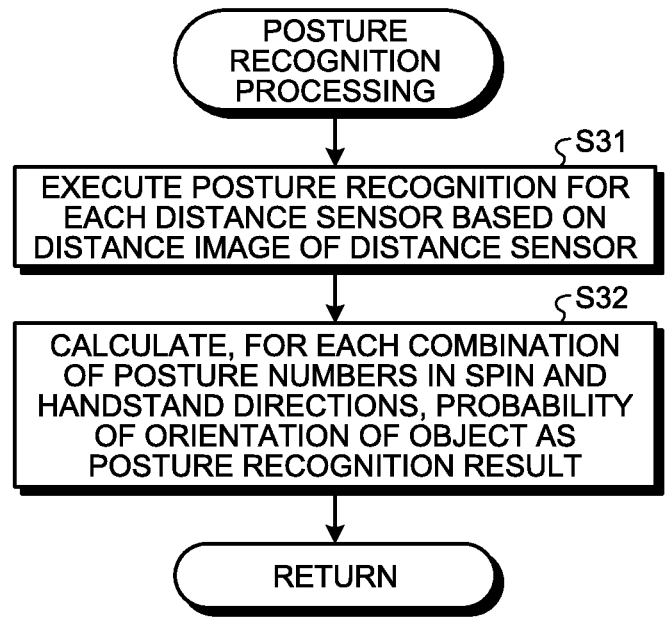
FIG. 29 is a flowchart illustrating exemplary posture recognition processing.

The following describes the posture recognition processing with reference to FIG. 29. FIG. 29 is a flowchart illustrating exemplary posture recognition processing.

The posture recognition unit 134 refers to the posture recognition dictionary storage unit 123 and executes the posture recognition for each distance sensor 10 based on the distance image of the distance sensor 10 (step S31). The posture recognition unit 134 calculates, for each combination of posture numbers in the spin and handstand directions, the probability of the orientation of the object as a posture recognition result (step S32), and returns to the original processing. Accordingly, the posture recognition unit 134 can recognize the orientation (posture) of the object.

In FIG. 26, when the posture recognition processing ends, the posture recognition unit 134 executes dictionary determination processing (step S4).

Figure 30:
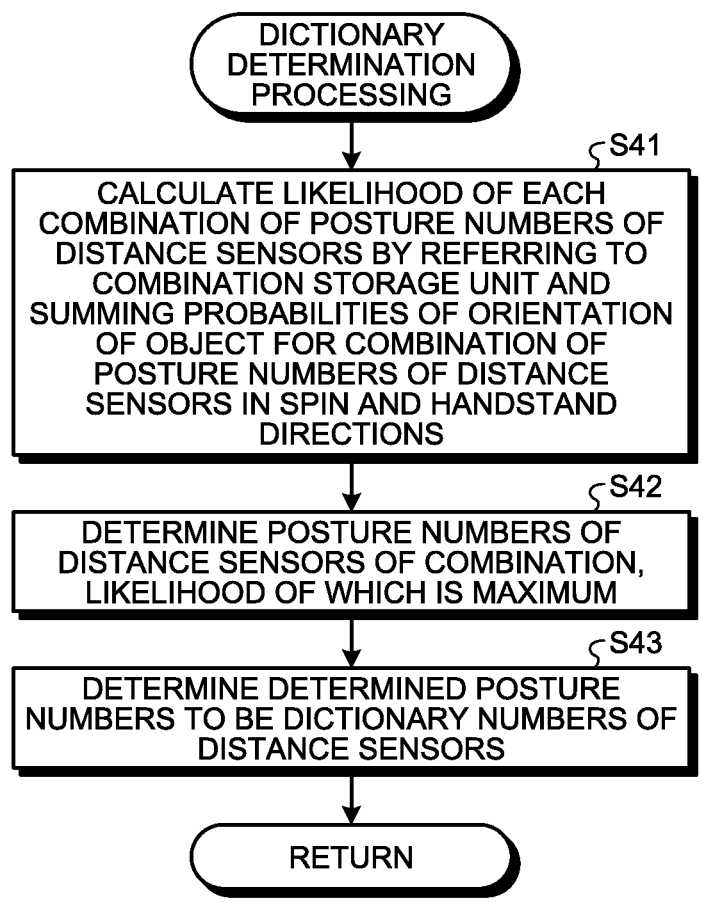
FIG. 30 is a flowchart illustrating exemplary dictionary determination processing.

The following describes the dictionary determination processing with reference to FIG. 30. FIG. 30 is a flowchart illustrating exemplary dictionary determination processing.

The posture recognition unit 134 calculates the likelihood of each combination of the posture numbers of the distance sensors 10 by referring to the combination storage unit 122 and summing the probabilities of the orientation of the object for the combination of the posture numbers of the distance sensors 10 in the spin and handstand directions (step S41).

The posture recognition unit 134 determines posture numbers of the distance sensors 10 of a combination, the likelihood of which is maximum (step S42). The posture recognition unit 134 determines the determined posture numbers to be dictionary numbers of the distance sensors 10 (step S43), and returns to the original processing. Accordingly, the posture recognition unit 134 can determine the dictionary number of the skeleton recognition dictionary used in the skeleton recognition.

In FIG. 26, the posture recognition unit 134 outputs the determined dictionary number of each distance sensor 10 to the estimation unit 135 (step S5). Accordingly, as a result of recognition of the posture of the person 5, the recognition device 100 can output the dictionary number of the skeleton recognition dictionary used for each distance sensor 10. Thus, the recognition device 100 can prevent decrease of the accuracy of classification of the orientation of the person 5 due to the occurrence of occlusion, in other words, the accuracy of recognition. In addition, the recognition device 100 can fast integrate the point group data based on the distance images of the distance sensors 10 and can accurately perform the posture recognition. In addition, the recognition device 100 can improve the accuracy of the posture recognition as compared to a case in which the number of distance sensors 10 is one. When the position of each distance sensor 10 is not changed, the positional relation calculation processing and the combination determination processing may be omitted in repetitive execution of the first recognition processing.

Figure 31:
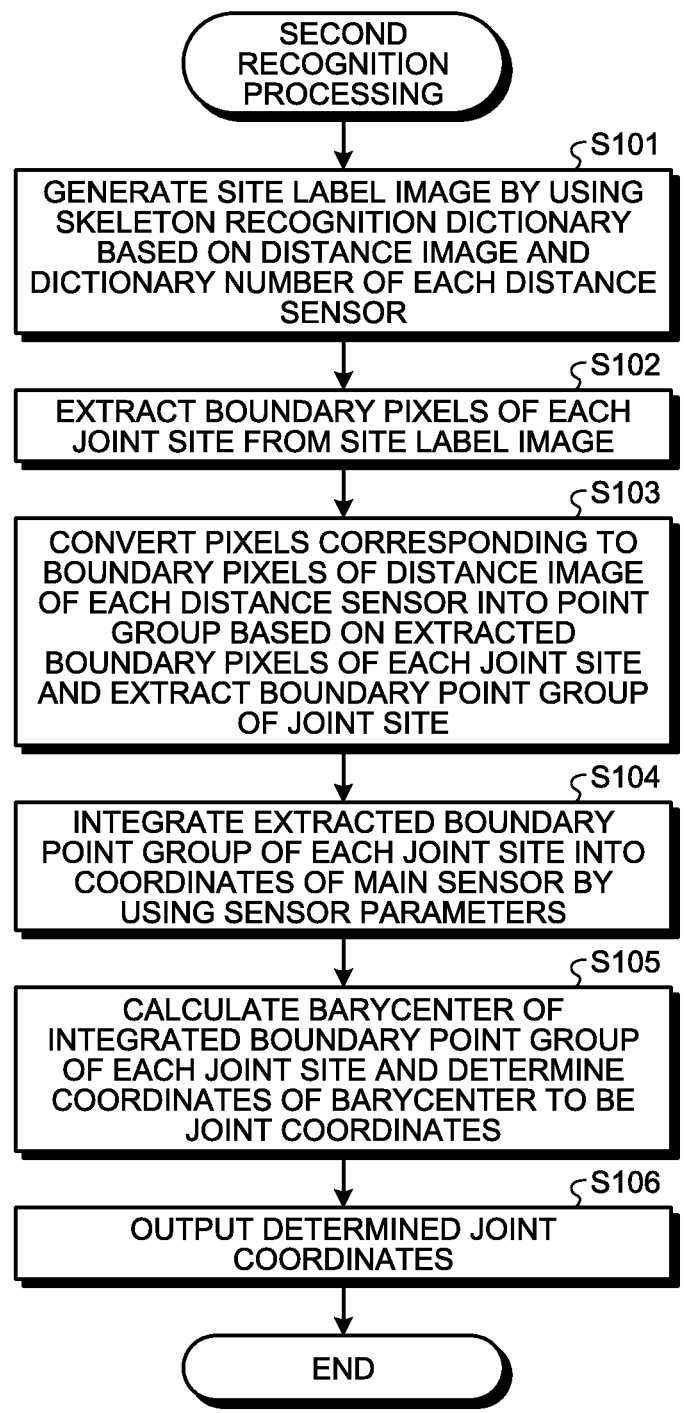
FIG. 31 is a flowchart illustrating exemplary second recognition processing according to the embodiment.

The following describes the second recognition processing of performing the skeleton recognition with reference to FIG. 31. FIG. 31 is a flowchart illustrating exemplary second recognition processing according to the embodiment.

The estimation unit 135 of the recognition device 100 receives inputting of each distance image from the acquisition unit 131 and inputting of the dictionary number of each distance sensor 10 from the posture recognition unit 134.

The estimation unit 135 refers to the skeleton recognition dictionary storage unit 124 and generates a site label image by using the skeleton recognition dictionary based on the distance image and dictionary number of each distance sensor 10 (step S101).

The estimation unit 135 extracts boundary pixels of each joint site from the generated site label image (step S102). The estimation unit 135 converts pixels corresponding to boundary pixels of the distance image of each distance sensor 10 into a point group based on the extracted boundary pixels of each joint site, and extracts the boundary point group of the joint site (step S103). The estimation unit 135 outputs the extracted boundary point group of each joint site of each distance sensor 10 to the second determination unit 136.

The second determination unit 136 refers to the positional relation storage unit 121 and integrates the extracted boundary point group of each joint site of each distance sensor 10, which is input from the estimation unit 135, into the coordinates of the main sensor 10a by using sensor parameters (step S104). The second determination unit 136 calculates the barycenter of the integrated boundary point group of each joint site and determines the coordinates of the barycenter to be joint coordinates (step S105). The second determination unit 136 outputs the determined joint coordinates to, for example, another processing unit or processing device (step S106). Accordingly, the recognition device 100 can prevent recognition accuracy decrease due to the occurrence of occlusion. In addition, the point group increase due to the distance sensors (n distance sensors) 10 can improve, by 1/sqrt(n) at maximum, the accuracy of fitting at a later stage in the skeleton recognition. In addition, the recognition device 100 can output a result of fast and highly accurate skeleton recognition.

In this manner, the recognition device 100 acquires the positional relation between the distance sensors 10 each of which senses the distance to the object. In addition, the recognition device 100 provisionally classifies the orientation of the object relative to each individual distance sensor 10 included in the distance sensors 10 into one of a plurality of classifications based on sensing data acquired by the individual distance sensor 10. In addition, the recognition device 100 calculates the likelihood of each combination corresponding to the positional relation between the distance sensors 10 based on result of the provisional classification of the orientation of the object relative to the individual distance sensor 10. In addition, the recognition device 100 classifies the orientation of the object corresponding to each individual sensor in accordance with the calculated likelihood of each combination. As a result, the recognition device 100 can prevent recognition accuracy decrease due to the occurrence of occlusion.

In addition, the recognition device 100 calculates the likelihood of each combination corresponding to the positional relation between the distance sensors 10 in the direction in which the object handstands and the direction in which the object spins. As a result, the recognition device 100 can prevent recognition accuracy decrease due to the occurrence of occlusion.

In addition, the recognition device 100 classifies the orientation of the object corresponding to each individual distance sensor 10 in accordance with likelihood as the sum of the likelihood of each individual distance sensor 10 corresponding to the combination. As a result, the accuracy of classification of the orientation of the object at each distance sensor 10 can be improved.

In addition, the recognition device 100 acquires the positional relation between the distance sensors 10 that sense distance to the object. In addition, the recognition device 100 acquires sensing data acquired by each individual distance sensor 10 included in the distance sensors 10. In addition, the recognition device 100 estimates the three-dimensional position of the skeleton of the object when viewed from each individual distance sensor 10 based on each acquired sensing data and the skeleton recognition dictionary selected in accordance with the orientation of the object relative to the individual distance sensor 10. In addition, the recognition device 100 determines the three-dimensional position of the skeleton of the object based on a result of the estimation of the three-dimensional position of the skeleton of the object when viewed from each individual distance sensor 10 and the positional relation between the distance sensors 10. As a result, the recognition device 100 can prevent recognition accuracy decrease due to the occurrence of occlusion.

In addition, the recognition device 100 generates, based on the sensing data, a site label image in which a site of the object is expressed by a site label by using the skeleton recognition dictionary. In addition, the recognition device 100 estimates the three-dimensional position of the skeleton of the object based on the site label in the generated site label image. As a result, the three-dimensional position of the skeleton of the object can be estimated for each distance sensor 10.

In addition, the recognition device 100 estimates the three-dimensional position of the skeleton of the object by using data of the vicinity of the boundary of the site label in the sensing data. As a result, the recognition device 100 can reduce the processing amount of conversion from the distance image to the point group data.

In addition, the recognition device 100 determines the barycenter of the boundaries of the site labels to be a joint position. As a result, the recognition device 100 can determine the joint position.

In addition, the recognition device 100 calculates the barycenter of the boundaries by using a result of estimation of the three-dimensional position of the skeleton when viewed from the distance sensor 10, the distance of which to the object is shortest among the distance sensors 10. As a result, the recognition device 100 can improve the accuracy of calculation of the barycenter of the boundaries.

In addition, the recognition device 100 calculates dispersion of data of the vicinity of the boundary for each individual distance sensor 10. In addition, the recognition device 100 estimates the three-dimensional position of the skeleton of the object by using sensing data obtained by randomly thinning or increasing the sensing data of each individual distance sensor 10 by using the reciprocal of the calculated dispersion. As a result, the recognition device 100 can improve the speed or accuracy of calculation of the barycenter of the boundaries.

In addition, the recognition device 100 determines the position of the site based on the determined joint positions. As a result, the recognition device 100 can determine the position of the site to be a position other than the barycenter of the boundaries of the site labels, such as the center between both shoulders.

In addition, the recognition device 100 determines the position of the site corresponding to the site label to be the centroid of the site label. As a result, the recognition device 100 can determine the position of the site to be a position, such as the head, other than the barycenter of the boundaries of the site labels.

In the above-described embodiment, the second recognition processing of performing the skeleton recognition is executed by using a result of the first recognition processing of performing the posture recognition, but the present invention is not limited thereto. For example, the skeleton recognition may be performed by executing the second recognition processing according to the present embodiment based on a result obtained by using another method in the posture recognition. Alternatively, the skeleton recognition may be performed by using another method based on a result of the posture recognition performed by executing the first recognition processing according to the present embodiment.

In the above-described embodiment, the person 5 performing gymnastics is measured when the posture recognition and the skeleton recognition are performed, but the present invention is not limited thereto. For example, the present invention is also applicable to check of movement in another scoring sport such as figure skating and in rehabilitation, and applicable to form analysis in baseball, golf, and the like.

In the above-described embodiment, the two axes in the spin and handstand directions of the person 5 are used, but the present invention is not limited thereto. For example, three axes additionally including a cartwheel direction may be used, or polar coordinates may be used in expression with the orientation of the backbone of the person 5 and three angles of rotation of a line connecting the shoulders.

Components of units illustrated in the drawings do not necessarily need to be physically configured as illustrated in the drawings. In other words, specific configurations of distribution and integration of the units are not limited to the illustrated configurations, but all or some of the components may be functional or physically distributed and integrated in optional units in accordance with various loads, use conditions, and the like. For example, the calculation unit 132, the first determination unit 133, and the posture recognition unit 134 may be integrated. The pieces of processing illustrated in the drawings are not limited to the above-described order, but may be simultaneously performed or may be performed in a different order without inconsistency of the processing contents.

All or an optional part of various kinds of processing functions performed by each device may be executed by a CPU (or GPU). Alternatively, all or an optional part of the various kinds of processing functions may be executed by a computer program analyzed and executed by the CPU (or GPU) or by wired logic hardware.

Figure 32:
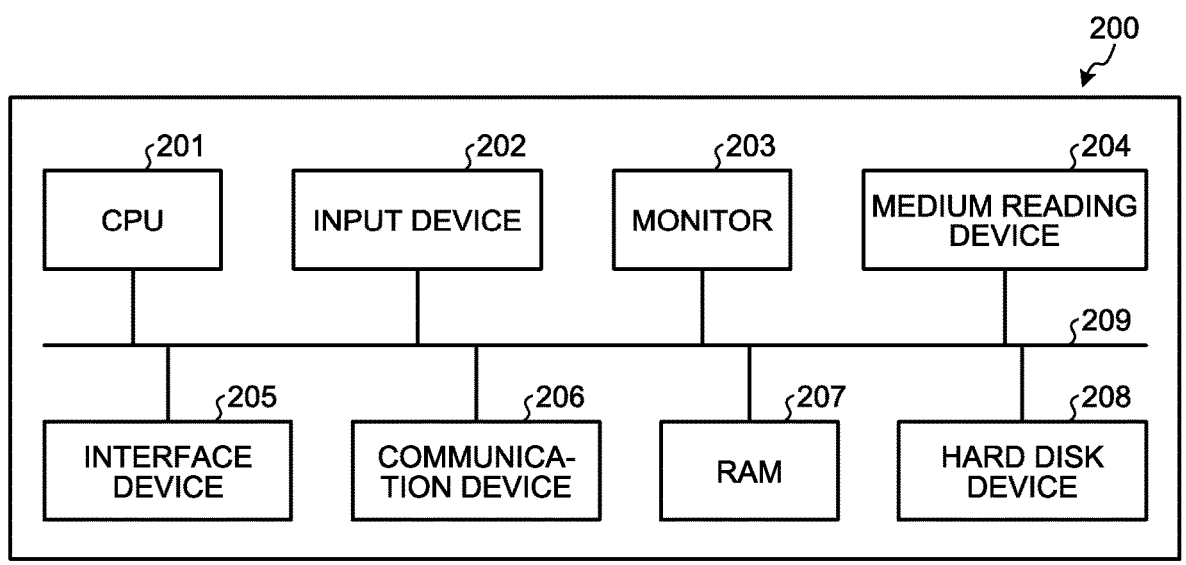
FIG. 32 is a diagram illustrating an exemplary computer that executes a recognition program.

The various kinds of processing described above in the embodiment can be achieved by a computer executing a computer program prepared in advance. Thus, the following describes an exemplary computer that executes a computer program having functions same as those in the above-described embodiment. FIG. 32 is a diagram illustrating an exemplary computer that executes a recognition program.

As illustrated in FIG. 32, a computer 200 includes a CPU 201 that executes various kinds of arithmetic processing, an input device 202 that receives data input, and a monitor 203. The computer 200 also includes a medium reading device 204 that reads a computer program and the like from a storage medium, an interface device 205 for connection with various devices, and a communication device 206 for connection with each distance sensor 10, another information processing device, or the like in a wired or wireless manner. The computer 200 also includes a RAM 207 that temporarily stores various kinds of information, and a hard disk device 208. The devices 201 to 208 are connected with a bus 209.

The hard disk device 208 stores the recognition program having functions same as those of the processing units of the acquisition unit 131, the calculation unit 132, the first determination unit 133, the posture recognition unit 134, the estimation unit 135, and the second determination unit 136 illustrated in FIG. 8. The hard disk device 208 also stores various kinds of data for achieving the positional relation storage unit 121, the combination storage unit 122, the posture recognition dictionary storage unit 123, the skeleton recognition dictionary storage unit 124, and the recognition program. For example, the input device 202 receives inputting of various kinds of information such as operation information from a user of the computer 200. For example, the monitor 203 displays various screens such as a display screen to the user of the computer 200. The interface device 205 is connected with, for example, a printing device. For example, the communication device 206 has functions same as those of the communication unit 110 illustrated in FIG. 8, is connected with each distance sensor 10 or another information processing device, and communicates various kinds of information with the distance sensor 10 or the other information processing device.

The CPU 201 performs various kinds of processing by reading each computer program stored in the hard disk device 208, loading the computer program onto the RAM 207, and executing the computer program. These computer programs can cause the computer 200 to function as the acquisition unit 131, the calculation unit 132, the first determination unit 133, the posture recognition unit 134, the estimation unit 135, and the second determination unit 136 illustrated in FIG. 8.

The above-described recognition program does not necessarily need to be stored in the hard disk device 208. For example, the program may be stored in a storage medium readable by the computer 200 and may be read and executed by the computer 200. Examples of the storage medium readable by the computer 200 include portable recording media such as a CD-ROM, a digital versatile disc (DVD), and a universal serial bus (USB) memory, a semiconductor memory such as a flash memory, and a hard disk drive. Alternatively, the recognition program may be stored in a device connected with a network such as a public line, the Internet, a LAN, or the like and may be read from the network and executed by the computer 200.

Recognition accuracy decrease due to the occurrence of occlusion can be prevented.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A recognition method executed by a processor, the recognition method comprising:

acquiring positional relation between a plurality of sensors each of which senses a distance to an object;

estimating a three-dimensional position of a skeleton of the object when viewed from each individual sensor included in the sensors based on sensing data acquired by the individual sensor and a skeleton recognition dictionary selected in accordance with an orientation of the object relative to the individual sensor, wherein the estimating includes generating a site label image in which a site of the object is labeled based on a distance thereto included in the sensing data, in the site label image a boundary of the site of the object corresponding to a joint site, the site being expressed by a site label by using the skeleton recognition dictionary, and estimating the three-dimensional position of the skeleton of the object based on the site label in the generated site label image; and determining three-dimensional position of the skeleton of the object based on a result of estimation of the three-dimensional position of the skeleton of the object when viewed from each individual sensor and the positional relation between the sensors.

2. The recognition method according to claim 1, wherein the estimating includes estimating the three-dimensional position of the skeleton of the object by using data corresponding to a boundary of the site label in the sensing data.

3. The recognition method according to claim 1, wherein the determining includes determining a barycenter of a boundary of the site label to be a joint position.

4. The recognition method according to claim 3, wherein the determining includes calculating the barycenter of the boundary by using the result of estimation of the three-dimensional position of the skeleton when viewed from a sensor that has the shortest distance to the object among the sensors.

5. The recognition method according to claim 2, wherein the estimating includes calculating dispersion of the data corresponding to the boundary for each individual sensor and estimating the three-dimensional position of the skeleton of the object by using sensing data obtained by randomly thinning or increasing the sensing data of each individual sensor by using reciprocal of the calculated dispersion.

6. The recognition method according to claim 3, wherein the determining includes determining a position of the site based on determined joint positions.

7. The recognition method according to claim 3, wherein the determining includes determining the barycenter of the site label to be a position of the site corresponding to the site label.

* * * * *